(12) United States Patent
Ni et al.

(10) Patent No.: US 6,448,044 B2
(45) Date of Patent: *Sep. 10, 2002

(54) DNA ENCODING HUMAN NATURAL KILLER CELL ACTIVATING FACTOR II

(75) Inventors: Jian Ni, Rockville; Haodong Li, Gaithersburg; Guo-Liang Yu, Darnestown; Reiner L. Gentz, Silver Spring, all of MD (US)

(73) Assignee: Human Genome Sciences, Inc., Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/832,488

(22) Filed: Apr. 3, 1997

Related U.S. Application Data

(60) Provisional application No. 60/014,796, filed on Apr. 3, 1996.

(51) Int. Cl.[7] .................. C12P 21/02; C12P 21/04; C07H 21/04; C12N 15/74

(52) U.S. Cl. ............... 435/69.5; 435/70.1; 435/71.1; 435/71.2; 435/252.3; 435/320.1; 435/471; 536/23.5

(58) Field of Search .................. 536/23.5; 435/69.5, 435/252.3, 320.1, 70.1, 71.1, 71.2, 471

(56) References Cited

U.S. PATENT DOCUMENTS

| | | | |
|---|---|---|---|
| 5,316,933 A | | 5/1994 | Yoshimatsu et al. |
| 5,350,836 A | * | 9/1994 | Kopchick et al. |
| 5,476,839 A | | 12/1995 | Scott et al. |
| 6,143,867 A | | 11/2000 | Akerblom |

FOREIGN PATENT DOCUMENTS

| | | |
|---|---|---|
| EP | 0357067 | 8/1989 |
| WO | WO 97/37022 | 10/1997 |

OTHER PUBLICATIONS

US 5,728,820, 3/1998, Akerblom (withdrawn)
Vukicevic et al. PNAS USA 93:9021–9026, 1996.*
Massague J. Cell 49:437–8, 1987.*
Pilbeam et al. Bone 14:717–720, 1993.*
Skolnick et al. Trends in Biotech. 18:34–39, 2000.*
Bork P. Genome Research 10:398–400, 2000.*
Doerks et al. Trends in Genetics 14:248–250, 1998.*
Smith et al. Nature Biotechnology 15:1222–1223, 1997.*
Brenner SE. Trends in Genetics 15:132–133, 1999.*
Bork et al. Trends in Genetics 12:425–427, 1996.*
Li et al., 1995, *J. Biochem.* 305:921–927.
Kita et al., 1995, *J. Immunology* 4749–4758.
Barker et al., 1991, *J. Clin. Invest.* 88:798–805.
Yoshimatsu et al., 1992, *Molecular Immun.* 29:537–546.
Kobayashi et al., 1991, *Microbiol. Immun.* 35:981–993.
Yamamoto et al., 1994, *Brit. J. Of Haematology*, 86:490–495.
Plager, et al., "A Novel and Highly Divergent Homolog of Human Eosinophil Granule Major Basic Protein," J. Biol. Chem., 274(20):14464–14473 (1999).

* cited by examiner

*Primary Examiner*—Gary L. Kunz
*Assistant Examiner*—Robert S. Landsman
(74) *Attorney, Agent, or Firm*—Human Genome Sciences, Inc.

(57) ABSTRACT

The invention relates to NKAF II polypeptides, polynucleotides encoding the polypeptides, methods for producing the polypeptides, in particular by expressing the polynucleotides, and agonists and antagonists of the polypeptides. The invention further relates to methods for utilizing such polynucleotides, polypeptides, agonists and antagonists for applications, which relate, in part, to research, diagnostic and clinical arts.

138 Claims, 3 Drawing Sheets

```
          10                    30                    50
CTTGGAAGGGGCTATACTAGACACACAAGACAGCCCCAAGAAGGACGGTGGAGTAGTGT 70                    90                   110
CCTCGCTAAAAGACAGTAGATATGCAACGCCTCTTGCTCCTGCCCTTTCTCCTGCTGGGA
                              M   Q   R   L   L   L   P   F   L   L   G 130                   150                   170
ACAGTTTCTGCTCTTCATCTGGAGAATGATGCCCCCATCTGGAGAGCCTAGAGACACAG
 T   V   S   A   L   H   L   E   N   D   A   P   H   L   E   S   L   E   T   Q 190                   210                   230
GCAGACCTAGGCCAGGATCTGGATAGTTCAAAGGAGCAGGAGAGAGACTTGGCTCTGACG
 A   D   L   G   Q   D   L   D   S   S   K   E   Q   E   R   D   L   A   L   T 250                   270                   290
GAGGAGGTGATTCAGGCAGAGGGAGAGGAGGTCAAGGCTTCTGCCTGTCAAGACAACTTT
 E   E   V   I   Q   A   E   G   E   E   V   K   A   S   A   C   Q   D   N   F 310                   330                   350
GAGGATGAGGAAGCCATGGAGTCGGACCCAGCTGCCTTAGACAAGGACTTCCAGTGCCCC
 E   D   E   E   A   M   E   S   D   P   A   A   L   D   K   D   F   Q   C   P 370                   390                   410
AGGGAAGAAGACATTGTTGAAGTGCAGGGAAGTCCAAGGTGCAAGACCTGCCGCTACTAT
 R   E   E   D   I   V   E   V   Q   G   S   P   R   C   K   T   C   R   Y   Y 430                   450                   470
TTGGTGCGGACTCCTAAAACTTTTGCAGAAGCTCAGATTGTCTGCAGCAGATGCTACGGA
 L   V   R   T   P   K   T   F   A   E   A   Q   I   V   C   S   R   C   Y   G 490                   510                   530
GGCAACCTTGTCTCTATCCATGACTTCAACTTCAACTATCGCATCATGTGCATCAGTAAC
 G   N   L   V   S   I   H   D   F   N   F   N   Y   R   I   M   C   I   S   N 550                   570                   590
ACAGTCAACCAAGCCCAGGTCTGGATTGGAGGCAACCTCAGGGGCTGGTTCCTGTGGAAG
 T   V   N   Q   A   Q   V   W   I   G   G   N   L   R   G   W   F   L   W   K 610                   630                   650
CGGTTTTGCTGGACTGATGGGAGCCACTGGAATTTTGCTTACTGGTCCCCAGGGCAACCT
 R   F   C   W   T   D   G   S   H   W   N   F   A   Y   W   S   P   G   Q   P 670                   690                   710
GGGAATGGGCAAGGCTCCTGTGTGGCCCTATGCACCAAAGGAGGTTATTGGCGACGAACT
 G   N   G   Q   G   S   C   V   A   L   C   T   K   G   G   Y   W   R   R   T 730                   750                   770
CAATGCGACAAGCAACTGCCCTTCGTCTGCTCCTTCTAAGCCAGCGGCACGGAGACCCTG
 Q   C   D   K   Q   L   P   F   V   C   S   F   *

790                   810                   830
CCAGCAGCTCCCTCCCGTCCCCCAACCTCTCCTGCTCATAAATCCAGACTTCCCACAGCA

850
AAAAAAAAAAAAAAAAA
```

FIG.1

```
  1 MQRLLLLPFLLLGTVSALHLENDAPHLESLETQADLGQDLDSSKEQERDL  50
    :|  ||    ||:|.||||||  .:..  :|.   ..  .|.:|  :...|||.:
  1 .mklplllallfgavsalhlrsetstfetplgaktlped.eetpeqemee  48

51 ALTEEVIQAEGEEVKASACQDNFEDEEAME...SDPAALDKDFQCPREEDI  98
    ..  |:     |:||  .:|:::|.   ..::|:|   |  |.  :||::  ||  |||.
 49 tpcrel...eeeeewgsgsedaskkdgavesisvpdmvdknltcpeeedt  95

99 VEVQGSPRCKTCRYYLVRTPKTFAEAQIVCSRCYGGNLVSIHDFNFNYRI 148
    |.|  |  |   |.||||.|||.  .||.:|  :.|.|||  ||||||:||:||||
 96 vkvvgipgcqtcryllvrslqtfsqawftcrrcyrgnlvsihnfninyri 145

149 MCISNTVNQAQVWIGGNLRGWFLWKRFCWTDGSHWNFAYWSPGQPGNGQG 198
    |   ..:||:||||||.: |.    :||  |.|||:||||||.:  ||  ..|
146 qcsvsalnqgqvwiggritgsgrcrrfqwvdgsrwnfaywaahqpwsrgg 195

199 SCVALCTKGGYWRRTQCDKQLPFVCSF. 225
    ||||||:||||||.:|  :.|||:||:|
196 hcvalctrggywrrahclrrlpficsy. 222
```

FIG.2

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 857 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 82..756

(ix) FEATURE:
      (A) NAME/KEY: sig_peptide
      (B) LOCATION: 82..130

(ix) FEATURE:
      (A) NAME/KEY: mat_peptide
      (B) LOCATION: 133..756

(xi) SEQUENCE DESCRIPTION: SEQ ID NO:1:

CTTGGAAGGG GCTATACTAG ACACACAAAG ACAGCCCCAA GAAGGACGGT GGAGTAGTGT    60

CCTCGCTAAA AGACAGTAGA T ATG CAA CGC CTC TTG CTC CTG CCC TTT CTC    111

```
                    Met Gln Arg Leu Leu Leu Pro Phe Leu
                    -17     -15             -10

CTG CTG GGA ACA GTT TCT GCT CTT CAT CTG GAG AAT GAT GCC CCC CAT    159
Leu Leu Gly Thr Val Ser Ala Leu His Leu Glu Asn Asp Ala Pro His
        -5                  1                   5

CTG GAG AGC CTA GAG ACA CAG GCA GAC CTA GGC CAG GAT CTG GAT AGT    207
Leu Glu Ser Leu Glu Thr Gln Ala Asp Leu Gly Gln Asp Leu Asp Ser
 10              15                  20                  25

TCA AAG GAG CAG GAG AGA GAC TTG GCT CTG ACG GAG GAG GTG ATT CAG    255
Ser Lys Glu Gln Glu Arg Asp Leu Ala Leu Thr Glu Glu Val Ile Gln
                 30                  35                  40

GCA GAG GGA GAG GAG GTC AAG GCT TCT GCC TGT CAA GAC AAC TTT GAG    303
Ala Glu Gly Glu Glu Val Lys Ala Ser Ala Cys Gln Asp Asn Phe Glu
                     45                  50                  55

GAT GAG GAA GCC ATG GAG TCG GAC CCA GCT GCC TTA GAC AAG GAC TTC    351
Asp Glu Glu Ala Met Glu Ser Asp Pro Ala Ala Leu Asp Lys Asp Phe
                         60                  65                  70

CAG TGC CCC AGG GAA GAA GAC ATT GTT GAA GTG CAG GGA AGT CCA AGG    399
Gln Cys Pro Arg Glu Glu Asp Ile Val Glu Val Gln Gly Ser Pro Arg
 75                  80                  85

TGC AAG ACC TGC CGC TAC TAT TTG GTG CGG ACT CCT AAA ACT TTT GCA    447
Cys Lys Thr Cys Arg Tyr Tyr Leu Val Arg Thr Pro Lys Thr Phe Ala
 90                  95                 100                 105

GAA GCT CAG ATT GTC TGC AGC AGA TGC TAC GGA GGC AAC CTT GTC TCT    495
Glu Ala Gln Ile Val Cys Ser Arg Cys Tyr Gly Gly Asn Leu Val Ser
                    110                 115                 120

ATC CAT GAC TTC AAC TTC AAC TAT CGC ATC ATG TGC ATC AGT AAC ACA    543
Ile His Asp Phe Asn Phe Asn Tyr Arg Ile Met Cys Ile Ser Asn Thr
                125                 130                 135

GTC AAC CAA GCC CAG GTC TGG ATT GGA GGC AAC CTC AGG GGC TGG TTC    591
Val Asn Gln Ala Gln Val Trp Ile Gly Gly Asn Leu Arg Gly Trp Phe
            140                 145                 150

CTG TGG AAG CGG TTT TGC TGG ACT GAT GGG AGC CAC TGG AAT TTT GCT    639
Leu Trp Lys Arg Phe Cys Trp Thr Asp Gly Ser His Trp Asn Phe Ala
155                 160                 165

TAC TGG TCC CCA GGG CAA CCT GGG AAT GGG CAA GGC TCC TGT GTG GCC    687
Tyr Trp Ser Pro Gly Gln Pro Gly Asn Gly Gln Gly Ser Cys Val Ala
170                 175                 180                 185

CTA TGC ACC AAA GGA GGT TAT TGG CGA CGA ACT CAA TGC GAC AAG CAA    735
Leu Cys Thr Lys Gly Gly Tyr Trp Arg Arg Thr Gln Cys Asp Lys Gln
                    190                 195                 200

CTG CCC TTC GTC TGC TCC TTC TAAGCCAGCG GCACGGAGAC CCTGCCAGCA       786
Leu Pro Phe Val Cys Ser Phe
                205

GCTCCCTCCC GTCCCCCAAC CTCTCCTGCT CATAAATCCA GACTTCCAC AGCAAAAAAA   846

AAAAAAAAA A                                                       857

(2) INFORMATION FOR SEQ ID NO:2:

(i) SEQUENCE CHARACTERISTICS:
        (A) LENGTH: 225 amino acids
        (B) TYPE: amino acid
        (D) TOPOLOGY: linear (ii) MOLECULE TYPE: protein (xi) SEQUENCE DESCRIPTION: SEQ ID NO:2:

Met Gln Arg Leu Leu Leu Pro Phe Leu Leu Leu Gly Thr Val Ser
-17     -15             -10                 -5

Ala Leu His Leu Glu Asn Asp Ala Pro His Leu Glu Ser Leu Glu Thr
```

```
           1               5                  10                 15
Gln Ala Asp Leu Gly Gln Asp Leu Asp Ser Ser Lys Glu Gln Glu Arg
                    20                 25                 30
Asp Leu Ala Leu Thr Glu Glu Val Ile Gln Ala Glu Gly Glu Glu Val
                35                 40                 45
Lys Ala Ser Ala Cys Gln Asp Asn Phe Glu Asp Glu Glu Ala Met Glu
            50                 55                 60
Ser Asp Pro Ala Ala Leu Asp Lys Asp Phe Gln Cys Pro Arg Glu Glu
        65                 70                 75
Asp Ile Val Glu Val Gln Gly Ser Pro Arg Cys Lys Thr Cys Arg Tyr
80                 85                 90                 95
Tyr Leu Val Arg Thr Pro Lys Thr Phe Ala Glu Ala Gln Ile Val Cys
                   100                105                110
Ser Arg Cys Tyr Gly Gly Asn Leu Val Ser Ile His Asp Phe Asn Phe
               115                 120                125
Asn Tyr Arg Ile Met Cys Ile Ser Asn Thr Val Asn Gln Ala Gln Val
           130                 135                140
Trp Ile Gly Gly Asn Leu Arg Gly Trp Phe Leu Trp Lys Arg Phe Cys
    145                150                155
Trp Thr Asp Gly Ser His Trp Asn Phe Ala Tyr Trp Ser Pro Gly Gln
160                165                170                175
Pro Gly Asn Gly Gln Gly Ser Cys Val Ala Leu Cys Thr Lys Gly Gly
               180                 185                190
Tyr Trp Arg Arg Thr Gln Cys Asp Lys Gln Leu Pro Phe Val Cys Ser
           195                 200                205
Phe
```

(2) INFORMATION FOR SEQ ID NO:3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CGCCCATGGA GAATGATGCC CCCCAT                                      26

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CGCAAGCTTC TCCGTGCCGC TGGCTTA                                  27

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CGCGGATCCG CCATCATGCA ACGCCTCTTG                                    30

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CGCGGTACCC TCCGTGCCGC TGGCTTA                                       27

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CGCGGATCCG CCATCATGCA ACGCCTCTTG                                    30

(2) INFORMATION FOR SEQ ID NO:8:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CGCTCTAGAT CAAGCGTAGT CTGGGACGTC GTATGGGTAG AAGGAGCAGA CGAA         54

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CGCGGATCCG CCATCATGCA ACGCCTCTTG                                    30

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
CGCGGTACCC TCCGTGCCGC TGGCTTA                                                    27
```

(2) INFORMATION FOR SEQ ID NO:11:

(i) SEQUENCE CHARACTERISTICS:
        (A) LENGTH: 222 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

```
Met Lys Leu Pro Leu Leu Leu Ala Leu Leu Phe Gly Ala Val Ser Ala
1               5                   10                  15

Leu His Leu Arg Ser Glu Thr Ser Thr Phe Glu Thr Pro Leu Gly Ala
            20                  25                  30

Lys Thr Leu Pro Glu Asp Glu Glu Thr Pro Glu Gln Glu Met Glu Glu
                35                  40                  45

Thr Pro Cys Arg Glu Leu Glu Glu Glu Glu Trp Gly Ser Gly Ser
        50                  55                  60

Glu Asp Ala Ser Lys Lys Asp Gly Ala Val Glu Ser Ile Ser Val Pro
65                  70                  75                  80

Asp Met Val Asp Lys Asn Leu Thr Cys Pro Glu Glu Asp Thr Val
                85                  90                  95

Lys Val Val Gly Ile Pro Gly Cys Gln Thr Cys Arg Tyr Leu Leu Val
                100                 105                 110

Arg Ser Leu Gln Thr Phe Ser Gln Ala Trp Phe Thr Cys Arg Arg Cys
            115                 120                 125

Tyr Arg Gly Asn Leu Val Ser Ile His Asn Phe Asn Ile Asn Tyr Arg
            130                 135                 140

Ile Gln Cys Ser Val Ser Ala Leu Asn Gln Gly Gln Val Trp Ile Gly
145                 150                 155                 160

Gly Arg Ile Thr Gly Ser Gly Arg Cys Arg Arg Phe Gln Trp Val Asp
                165                 170                 175

Gly Ser Arg Trp Asn Phe Ala Tyr Trp Ala Ala His Gln Pro Trp Ser
            180                 185                 190

Arg Gly Gly His Cys Val Ala Leu Cys Thr Arg Gly Gly Tyr Trp Arg
            195                 200                 205

Arg Ala His Cys Leu Arg Arg Leu Pro Phe Ile Cys Ser Tyr
            210                 215                 220
```

DNA ENCODING HUMAN NATURAL KILLER CELL ACTIVATING FACTOR II

This application claims benefit under 35 U.S.C. §119(e) to U.S. Provisional Application Serial No. 60/014,796, filed Apr. 3, 1996.

FIELD OF THE INVENTION

This invention relates, in part, to newly identified polynucleotides and polypeptides; variants and derivatives of the polynucleotides and polypeptides; processes for making the polynucleotides and the polypeptides, and their variants and derivatives; agonists and antagonists of the polypeptides; and uses of the polynucleotides, polypeptides, variants, derivatives, agonists and antagonists. In particular, in these and in other regards, the invention relates to polynucleotides and polypeptides of human Natural Killer Cell Activating Factor II, sometimes hereinafter referred to as "NKAF II".

BACKGROUND OF THE INVENTION

The polypeptide of the present invention is a member of the natural killer cell activating factor (NKAF) family and shows homology to NKAF and human eosinophil; major basic protein. Natural killer cells (NK cells) show a destructive effect on specific cancer cells. Lymphokines affecting the activity of these NK cells have therefore attracted attention. It is reported that interleukin-2 and interferon enhance the activity of NK cells (Herberman, R. B., et al., *Immunol. Rev.*, 44:13 (1979); Vose, B. M., et al., *J. Immunol.* 130:768 (1983) and Domzig, W. etal., *J. Immunol.*, 130:1970(1983)).

NK cells are proposed to function as natural surveillance to deter cancer development in the body (Whiteside, T. and Herberman, R. B., *Clin. Immunol. Immunopathol* 58:1–23 (1989) and Trinchieri, G., *Adv. Immunol* 47:187–376 (1989)). NK cells are also important in controlling viral infection and the regulation of hematopoiesis (Trichieri, G., *Adv. Immunol.*, 47:187–376 (1989); Kiessling, R., et al.,*Eur. J. Immunol.* 7:655–663 (1977)).

The following facts indicate that NK cells play important roles in the host defense against cancer. Namely, a nude mouse lacking T cells by having a high NK activity does not always suffer from spontaneous or chemically induced carcinogenesis at a high frequency (Rygaard, J. et al.,*Immunol. Rev.*, 28:43 (1975); Stutman, D., et al., *Science,* 183:534 (1974)); and the metastasis of transplanted cancer cells is promoted in a beige mouse having T cells but a genetically low NK activity (Shimamura, K. and Tamaoki, K., *Jikken Igaku,* 2:398 (1984); James E. Talmadge, et al., *Nature,* 284:622 (1980)) and a mouse having an artificially lowered NK activity (Shimamura, supra).

Human eosinophil major basic protein (MBP) has a nearly identical sequence to that of known natural killer cell activating factor I. Human MBP is one of the principal mediators of injury to parasites in tissues in allergic inflammation. MBP is stored in eosinophil crystalloid granules and released with other granule constituents during eosinophil activation. MBP has no recognized enzymatic activity but it is toxic for some helminths (Ackerman, S. J. et al., *Am. J. Trop. Med. Hyg.,* 34:735–745 (1985)) and mammalian cells (Barker, R. L. et al., *J. Clin. Invest.* 88:798–805(1991)) in vitro. MBP is expressedprincipallyin bonemarroweosinophils, but it is also synthesized in basophils and placental trophoblast x-cells (Wasmoen, T. L. et al.,*J. Exp. Med.,* 170:2051–2063(1989)).

MBP stimulates the effector function of a wide variety of cells, namely MBP stimulates the noncytolytic release of histamine from human basophils and rat mass cells (O'Donnell, M. A. et al., *J. Exp. Med.* 157:1981 (1983)). MBP also stimulates neutrophils to release superoxide and ion and lysozyme, but not beta-glucuronidase or lactic dehydrogenase, and MBP enhances the expression of CR3 and P150, 95 by neutrophils. This indicates that MBP activates other cells associated with inflammation, such as basophils, platelets and neutrophils. The effector mechanisms may play a role in pathophysiology of various diseases where granule proteins are released. For example, MBP has been thought a cause for increased airway responsiveness, for example, bronchial asthma.

The effects of the natural killer cell activating factors are varied and influence numerous functions, both normal and abnormal, in the biological processes of the mammalian system. There is a clear need, therefore, for identification and characterization of proteins that influence biological activity, both normally and in diseased states. In particular, there is a need to isolate and characterize additional natural killer cell activating factors akin to known natural killer cell activating factors which may be employed, therefore, for preventing, ameliorating or correcting disfunctions or disease or augmenting positive natural actions of such receptors.

SUMMARY OF THE INVENTION

Toward these ends, and others, it is an object of the present invention to provide polypeptides, inter alia, that have been identified as novel NKAF II by homology between the amino acid sequence set out in FIG. 1 (SEQ ID NO:1 and 2) and known amino acid sequences of other proteins such as human eosinophil granule major basic protein.

It is a further object of the invention, moreover, to provide polynucleotides that encode NKAF II, particularly polynucleotidesthat encode the polypeptide herein designated NKAF II.

In a particularly preferred embodiment of this aspect of the invention the polynucleotide comprises the region encoding human NKAF II in the sequence set out in FIG. 1 (SEQ ID NO:2).

In accordance with this aspect of the present invention there is provided an isolated nucleic acid molecule encoding a mature polypeptide expressed by the human cDNA contained in ATCC Deposit No. 97465.

In accordance with this aspect of the invention there are provided isolated nucleic acid molecules encoding human NKAF II, including mRNAs, cDNAs, genomic DNAs and, in further embodiments of this aspect of the invention, biologically, diagnostically, clinically or therapeutically useful variants, analogs or derivatives thereof, or fragments thereof, including fragments of the variants, analogs and derivatives.

Among the particularly preferred embodiments of this aspect of the invention are naturally occurring allelic variants of human NKAF II.

It also is an object of the invention to provide NKAF II polypeptides, particularly human NKAF II polypeptides, that inhibit the growth of leukemia cells, to treat viral infection, to augment the effects of natural killer protein to treat neoplasias such as tumors and cancers, to prevent inflammation, to treat parasitic infection, to regulate hematopoiesis, to prevent damage from superoxide radicals in the body, for example, tissue injury and aging and to enhance an immunological response.

In accordance with this aspect of the invention there are provided novel polypeptides of human origin referred to herein as NKAF II as well as biologically, diagnostically or therapeutically useful fragments, variants and derivatives thereof, variants and derivatives of the fragments, and analogs of the foregoing.

Among the particularly preferred embodiments of this aspect of the invention are variants of human NKAF II encoded by naturally occurring alleles of the human NKAF II gene.

It is another object of the invention to provide a process for producing the aforementioned polypeptides, polypeptide fragments, variants and derivatives, fragments of the variants and derivatives, and analogs of the foregoing. In a preferred embodiment of this aspect of the invention there are provided methods for producing the aforementioned NKAF II polypeptides comprising culturing host cells having expressibly incorporated therein an exogenously-derivedhuman NKAF II-encoding polynucleotide under conditions for expression of human NKAF II in the host and then recovering the expressed polypeptide.

In accordance with another object the invention there are provided products, compositions, processes and methods that utilize the aforementioned polypeptides and polynucleotides for research, biological, clinical and therapeutic purposes, inter alia.

In accordance with certain preferred embodiments of this aspect of the invention, there are provided products, compositions and methods, inter alia, for, among other things: assessing NKAF II expression in cells by determining NKAF II polypeptides or NKAF II-encoding mRNA; assaying genetic variation and aberrations, such as defects, in NKAF II genes; and administering a NKAF II polypeptide or polynucleotide to an organism to augment NKAF II function or remediate NKAF II dysfunction.

In accordance with certain preferred embodiments of this and other aspects of the invention there are provided probes that hybridize to human NKAF II sequences.

In certain additional preferred embodiments of this aspect of the invention there are provided antibodies against NKAF II polypeptides. In certain particularly preferred embodiments in this regard, the antibodies are highly selective for human NKAF II. In accordance with another aspect of the present invention, there are provided NKAF II agonists. Among preferred agonists are molecules that mimic NKAF II, that bind to NKAF II-binding molecules or receptor molecules, and that elicit or augment NKAF II-induced responses. Also among preferred agonists are molecules that interact with NKAF II or NKAF II polypeptides, or with other modulators of NKAF II activities, and thereby potentiate or augment an effect of NKAF II or more than one effect of NKAF II.

In accordance with yet another aspect of the present invention, there are provided NKAF II antagonists. Among preferred antagonists are those which mimic NKAF II so as to bind to NKAF II receptor or binding molecules but not elicit a NKAF II-induced response or more than one NKAF II-induced response. Also among preferred antagonists are molecules that bind to or interact with NKAF II so as to inhibit an effect of NKAF II or more than one effect of NKAF II or which prevent expression of NKAF II.

The agonists and antagonists may be used to mimic, augment or inhibit the action of NKAF II polypeptides. They may be used, for instance, to inhibit the action of such polypeptides, for example, to prevent allergic inflammation, hypersensitivity, bronchial asthma, eosinophilia, chronic urticaria, atopic dermatitis, Kimura's disease and bone marrow transplant rejection.

In a further aspect of the invention there are provided compositions comprising a NKAF II polynucleotide or a NKAF II polypeptide for administration to cells in vitro, to cells ex vivo and to cells in vivo, or to a multicellular organism. In certain particularly preferred embodiments of this aspect of the invention, the compositions comprise a NKAF II polynucleotide for expression of a NKAF II polypeptide in a host organism for treatment of disease. Particularly preferred in this regard is expression in a human patient for treatment of a dysfunction associated with aberrant endogenous activity of NKAF II.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIG. 1 shows the nucleotide and deduced amino acid sequence of human NKAF II. The determined leader sequence is underlined.

FIG. 2 shows the regions of similarity between amino acid sequences of NKAF II and human eosinophil granule major basic protein polypeptides.

GLOSSARY

Figure 3:
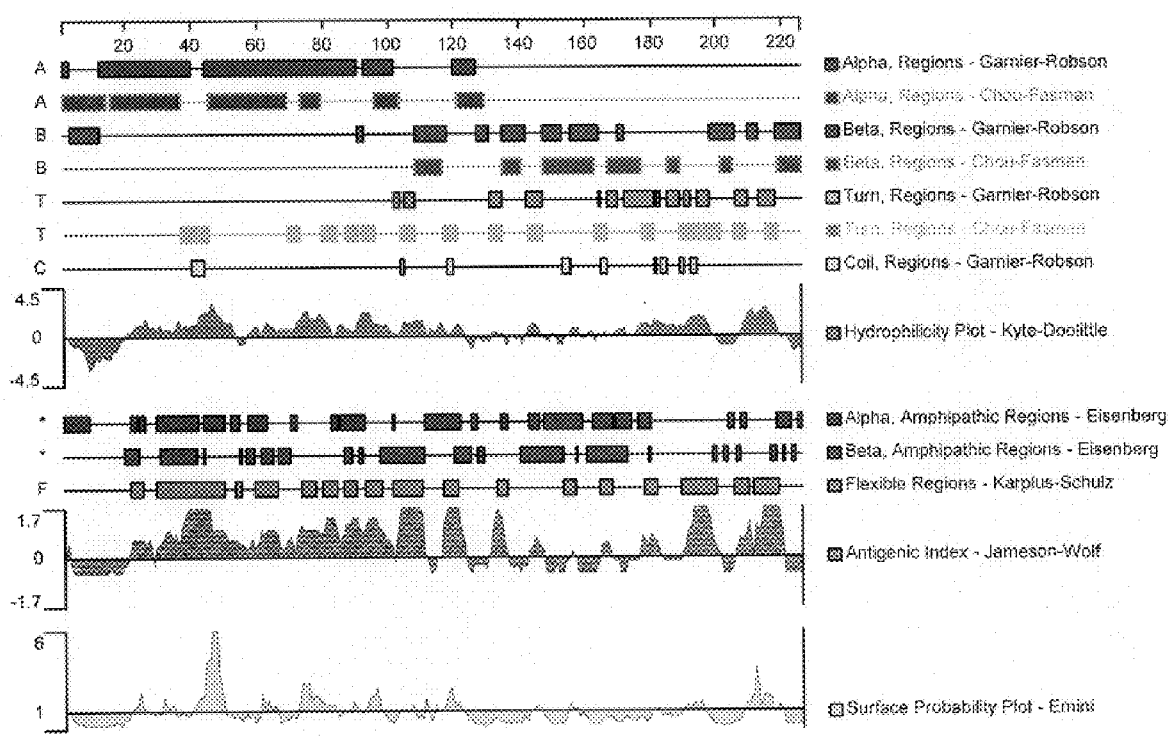
FIG. 3 shows structural and functional features of NKAF II deduced by the indicated techniques, as a function of amino acid sequence.

The following illustrative explanations are provided to facilitate understanding of certain terms used frequently herein, particularly in the examples. The explanations are provided as a convenience and are not limitative of the invention.

DIGESTION of DNA refers to catalytic cleavage of the DNA with a restriction enzyme that acts only at certain sequences in the DNA. The various restriction enzymes referred to herein are commercially available and their reaction conditions, cofactors and other requirements for use are known and routine to the skilled artisan.

For analytical purposes, typically, 1 mg of plasmid or DNA fragment is digested with about 2 units of enzyme in about 20 ml of reaction buffer. For the purpose of isolating DNA fragments for plasmid construction, typically 5 to 50 mg of DNA are digested with 20 to 250 units of enzyme in proportionately larger volumes.

Appropriate buffers and substrate amounts for particular restriction enzymes are described in standard laboratory manuals, such as those referenced below, and they are specified by commercial suppliers.

Incubation times of about 1 hour at 37° C. are ordinarily used, but conditions may vary in accordance with standard procedures, the supplier's instructions and the particulars of the reaction. After digestion, reactions may be analyzed, and fragments may be purified by electrophoresis through an agarose or polyacrylamide gel, using well known methods that are routine for those skilled in the art.

GENETIC ELEMENT generally means a polynucleotide comprising a region that encodes a polypeptide or a region that regulates transcription or translation or other processes important to expression of the polypeptide in a host cell, or a polynucleotide comprising both a region that encodes a polypeptide and a region operably linked thereto that regulates expression.

Genetic elements may be comprised within a vector that replicates as an episomal element; that is, as a molecule physically independent of the host cell genome. They may be comprised within mini-chromosomes, such as those that arise during amplification of transfected DNA by methotrexate selection in eukaryotic cells. Genetic elements also may be comprised within a host cell genome; not in their natural state but, rather, following manipulation such as isolation, cloning and introduction into a host cell in the form of purified DNA or in a vector, among others.

ISOLATED means altered "by the hand of man" from its natural state; i.e., that, if it occurs in nature, it has been changed or removed from its original environment, or both.

For example, a naturally occurring polynucleotide or a polypeptide naturally present in a living animal in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

LIGATION refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., MOLECULAR CLONING, A LABORATORY MANUAL, 2nd Ed.; Cold Spring Harbor Laboratory Press, Cold Spring Harbor, N.Y. (1989) and Maniatis et al., pg. 146, as cited below.

OLIGONUCLEOTIDE(S) refers to relatively short polynucleotides. Often the term refers to single-stranded deoxyribonucleotides, but it can refer as well to single-or double-stranded ribonucleotides, RNA:DNA hybrids and double-stranded DNAs, among others.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP.

The 3' end of a chemically synthesized oligonucleotide generally has a free hydroxyl group and, in the presence of a ligase, such as T4 DNA ligase, readily will form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

PLASMIDS generally are designated herein by a lower case p preceded and/or followed by capital letters and/or numbers, in accordance with standard naming conventions that are familiar to those of skill in the art. Starting plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

POLYNUCLEOTIDE(S) generally refers to any polyribonucleotide or polydeoxribonucleotide, which may be unmodified RNA or DNA or modified RNA or DNA. Thus, for instance, polynucleotides as used herein refers to, among others, single-and double-stranded DNA, DNA that is a mixture of single-and double-stranded regions, single- and double-stranded RNA, and RNA that is mixture of single-and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

POLYPEPTIDES, as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art.

Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance PROTEINS—STRUCTURE AND MOLECULAR PROPERTIES, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in POST-TRANSLATIONAL COVALENT MODIFICATION OF PROTEINS, B. C. Johnson, Ed., Academic Press, New York (1983); Seifter et al., Analysis for protein modifications and nonprotein cofactors, Meth. Enzymol. 182: 626–646 (1990) and Rattan et al., Protein Synthesis: Posttranslational Modifications and Aging, Ann. N.Y. Acad. Sci. 663: 48–62 (1992).

It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli*, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as *E. coli*. Accordingly, when glycosylation is desired, a polypeptide should be expressed in a glycosylating host, generally a eukaryotic cell. Insect cell often carry out the same post-translational glycosylations as mammalian cells and, for this reason, insect cell expression systems have been developed to express efficiently mammalian proteins having native patterns of glycosylation, inter alia. Similar considerations apply to other modifications.

It will be appreciated that the same type of modification may be present in the same or varying degree at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

VARIANT(S) of polynucleotides or polypeptides, as the term is used herein, are polynucleotides or polypeptides that differ from a reference polynucleotide or polypeptide, respectively. Variants in this sense are described below and elsewhere in the present disclosure in greater detail.

(1) A polynucleotide that differs in nucleotide sequence from another, reference polynucleotide. Generally, differences are limited so that the nucleotide sequences of the reference and the variant are closely similar overall and, in many regions, identical.

As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below.

(2) A polypeptide that differs in amino acid sequence from another, reference polypeptide. Generally, differences are limited so that the sequences of the reference and the variant are closely similar overall and, in many region, identical.

A variant and reference polypeptide may differ in amino acid sequence by one or more substitutions, additions, deletions, fusions and truncations, which may be present in any combination.

RECEPTOR MOLECULE, as used herein, refers to molecules which bind or interact specifically with NKAF II polypeptides of the present invention, including not only classic receptors, which are preferred, but also other molecules that specifically bind to or interact with polypeptides of the invention (which also may be referred to as "binding molecules" and "interaction molecules," respectively and as "NKAF II binding molecules" and "NKAF II interaction molecules." Binding between polypeptides of the invention and such molecules, including receptor or binding or interaction molecules may be exclusive to polypeptides of the invention, which is very highly preferred, or it may be highly specific for polypeptides of the invention, which is highly preferred, or it may be highly specific to a group of proteins that includes polypeptides of the invention, which is preferred, or it may be specific to several groups of proteins at least one of which includes polypeptides of the invention.

Receptors also may be non-naturally occurring, such as antibodies and antibody-derived reagents that bind specifically to polypeptides of the invention.

DESCRIPTION OF THE INVENTION

The present invention relates to novel NKAF II polypeptides and polynucleotides, among other things, as described in greater detail below. In particular, the invention relates to polypeptides and polynucleotides of a novel human NKAF II, which is related by amino acid sequence homology to human eosinophil granule major basic protein. The invention relates especially to NKAF II having the nucleotide and amino acid sequences set out in FIG. 1 (SEQ ID NO:1 and 2), and to the NKAF II nucleotide and amino acid sequences of the human cDNA in ATCC Deposit No. 97465 which is herein referred to as "the deposited clone" or as the "cDNA of the deposited clone." It will be appreciated that the nucleotide and amino acid sequences set out in FIG. 1 (SEQ ID NO:2) were obtained by sequencing the human cDNA of the deposited clone. Hence, the sequence of the deposited clone is controlling as to any discrepancies between the two and any reference to the sequence of FIG. 1 (SEQ ID NO:1) includes reference to the sequence of the human cDNA of the deposited clone.

Polynucleotides

In accordance with one aspect of the present invention, there are provided isolated polynucleotidesthat encode the NKAF II polypeptide having the deduced amino acid sequence of FIG. 1 (SEQ ID NO:2).

Using the information provided herein, such as the polynucleotide sequence set out in FIG. 1 (SEQ ID NO:1), a polynucleotide of the present invention encoding a human NKAF II polypeptide may be obtained using standard cloning and screening procedures, such as those for cloning cDNAs using mRNA from cells of human tissue as starting material. Illustrative of the invention, the polynucleotide set out in FIG. 1 (SEQ ID NO:1) was discovered in a cDNA library derived from cells of human bone marrow and fetal liver.

Human NKAF II of the invention is structurally related to other proteins of the human natural killer cell family, as shown by the results of sequencing the human cDNA encoding human NKAF II in the deposited clone. The human cDNA sequence thus obtained is set out in FIG. 1 (SEQ ID NO:1). It contains an open reading frame encoding a protein of about 225 amino acid residues. NKAF II has a deduced molecular weight of about 25.5 kDa; an isoelectric point of 4.661 and a –11.752 charge at pH of 7.0. The protein exhibits greatest homology to human eosinophil granule major basic protein among known proteins. NKAF II of FIG. 1 (SEQ ID NO:2) has about 65.8% similarity and about 50.2% identity with the amino acid sequence of human eosinophil granule major basic protein and NKAF as disclosed in U.S. Pat. No. 5,316,933.

The amino acid sequence of the complete NKAF II protein includes a leader sequence and a mature protein. More in particular, the present invention provides nucleic acid molecules encoding a mature form of the NKAF II protein. Thus, according to the signal hypothesis, once export of the growing protein chain across the rough endoplasmic reticulum has been initiated, proteins secreted by mammalian cells have a signal or secretory leader sequence which is cleaved from the complete polypeptide to produce a secreted "mature" form of the protein. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature NKAF II polypeptide having the amino acid sequence encoded by the cDNA clone contained in the host identified as ATCC Deposit No.97465. By the "mature NKAF II polypeptidehaving the amino acid sequence encoded by the cDNA clone in ATCC Deposit No. 97465" is meant the mature form(s) of the NKAF II protein produced by expression in a mammalian cell (e.g., COS cells, as described below) of the complete open reading frame encoded by the human DNA sequence of the clone contained in the vector in the deposited host.

In addition, methods for predicting whether a protein has a secretory leader as well as the cleavage point for that leader sequence are available. For instance, the method of McGeoch (*Virus Res.* 3:271–286 (1985)) uses the information from a short N-terminal charged region and a subsequent uncharged region of the complete (uncleaved) protein. The method of von Heinje (*Nucleic Acids Res.* 14:4683–4690 (1986)) uses the information from the residues surrounding the cleavage site, typically residues –13 to +2 where +1 indicates the amino terminus of the mature protein. The accuracy of predicting the cleavage points of known mammalian secretory proteins for each of these methods is in the range of 75–80% (von Heinje, supra). However, the two methods do not always produce the same predicted cleavage point(s) for a given protein.

In the present case, the deposited cDNA has been expressed in a baculovirus vector in insect cells as described hereinbelow, and amino acid sequencing of the amino terminus of the secreted species indicated that the mature NKAF II protein comprises amino acids 1 to 208 of SEQ ID NO:2. Thus, the leader sequence of the NKAF II protein in the amino acid sequence of SEQ ID NO:2 is 17 amino acids, from position –17 to –1.

More in particular the invention includes polypeptides comprising amino acids:. 14 to 225, 15 to 225, 16 to 225, 17 to 225, 18 to 225, 19 to 225, 20 to 225, 21 to 225, 22 to 225, and 23 to 225, all of SEQ ID NO:2. Polynucleotides encoding such polypeptides are also provided.

Polynucleotides of the present invention may be in the form of RNA, such as mRNA, or in the form of DNA, including, for instance, cDNA and genomic DNA obtained by cloning or produced by chemical synthetic techniques or by a combination thereof The DNA may be double-stranded or single-stranded. Single-stranded DNA may be the coding strand, also known as the sense strand, or it may be the non-coding strand, also referred to as the anti-sense strand.

The coding sequence which encodes the polypeptide may be identical to the coding sequence of the polynucleotide shown in FIG. 1 (SEQ ID NO:1). It also may be a polynucleotide with a different sequence, which, as a result of the redundancy (degeneracy) of the genetic code, encodes the polypeptide of the DNA of FIG. 1 (SEQ ID NO:1).

Polynucleotides of the present invention which encode the polypeptide of FIG. 1 (SEQ ID NO:2) may include, but are not limited to the coding sequence for the mature polypeptide, by itself; the coding sequence for the mature polypeptide and additional coding sequences, such as those encoding a leader or secretory sequence, such as a pre-, or pro- or prepro- protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al., Proc. Natl. Acad. Sci., USA 86: 821–824 (1989), for instance, hexa-histidineprovides for convenient purification of the fusion protein.

The HA tag corresponds to an epitope derived of influenza hemagglutinin protein, which has been described by Wilson et al., Cell 37: 767 (1984), for instance.

In accordance with the foregoing, the term "polynucleotide encoding a polypeptide" as used herein encompasses polynucleotides which include a sequence encoding a polypeptide of the present invention, particularly the human NKAF II having the amino acid sequence set out in FIG. 1 (SEQ ID NO:2). The term encompasses polynucleotides that include a single continuous region or discontinuous regions encoding the polypeptide (for example, interrupted by introns) together with additional regions.

The present invention further relates to variants of the herein above described polynucleotides which encode for fragments, analogs and derivatives of the polypeptide having the deduced amino acid sequence of FIG. 1 (SEQ ID NO:2). A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence of NKAF II set out in FIG. 1 (SEQ ID NO:2); variants, analogs, derivatives and fragments thereof, and fragments of the variants, analogs and derivatives.

Further particularly preferred in this regard are polynucleotides encoding NKAF II variants, analogs, derivatives and fragments, and variants, analogs and derivatives of the fragments, which have the amino acid sequence of the NKAF II polypeptide of FIG. 1 (SEQ ID NO:2) in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the NKAF II. Also especially preferred in this regard are conservative substitutions. Most highly preferred are polynucleotides encoding polypeptides having the amino acid sequence of FIG. 1 (SEQ ID NO:2) without substitutions.

Further preferred embodiments of the invention are polynucleotidesthat are at least 70% identical to a polynucleotide encoding the NKAF II polypeptide having the amino acid sequence set out in FIG. 1 (SEQ ID NO:2), and polynucleotides which are complementary to such polynucleotides. Alternatively, most highly preferred are polynucleotides that comprise a region that is at least 80% identical to a polynucleotide encoding the NKAF II polypeptide and polynucleotidescomplementarythereto. In this regard, polynucleotidesat least 90% identical to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Particularly preferred embodiments in this respect, moreover, are polynucleotides which encode polypeptides which retain substantially the same biological function or activity as the mature polypeptide encoded by the human cDNA of FIG. 1 (SEQ ID NO:1).

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention as discussed above, may be used as a hybridization probe for cDNA and genomic DNA to isolate full-length cDNAs and genomic clones encoding NKAF II and to isolate cDNA and genomic clones of other genes that have a high sequence similarity to the human NKAF II gene. Such probes generally will comprise at least 15 bases. Preferably, such probes will have at least 30 bases and may have at least 50 bases. Particularly preferred probes will have at least 30 bases and will have 50 bases or less.

For example, the coding region of the NKAF II gene may be isolated by screening using the known DNA sequence to synthesize an oligonucleotide probe. A labeled oligonucleotide having a sequence complementary to that of a gene of the present invention is then used to screen a library of human cDNA, genomic DNA or mRNA to determine which members of the library the probe hybridizes to.

The polynucleotides and polypeptides of the present invention may be employed as research reagents and materials for discovery of treatments and diagnostics to human disease, as further discussed herein relating to polynucleotide assays, inter alia.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may facilitate protein trafficking, may prolong or shorten protein half-life or may facilitate manipulation of a protein for assay or production, among other things. As generally is the case in situ, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Deposited Materials

A deposit containing a human NKAF II cDNA has been deposited with the American Type Culture Collection, as noted above. Also as noted above, the cDNA deposit is referred to herein as "the deposited clone" or as "the cDNA of the deposited clone."

The deposited clone was deposited with the American Type Culture Collection, 10801 University Boulvard Manassas, Va. 20110-2209, USA, on Mar. 6, 1996 and Deposit No. 97465.

The deposited material is a pBluescript SK (−) plasmid (Stratagene, La Jolla, Calif.) that contains the full length NKAF II cDNA, referred to as "PF266" upon deposit.

The deposit has been made under the terms of the Budapest Treaty on the international recognition of the deposit of micro-organisms for purposes of patent procedure. The strain will be irrevocably and without restriction or condition released to the public upon the issuance of a patent. The deposit is provided merely as convenience to those of skill in the art and is not an admissionthat a deposit is required for enablement, such as that required under 35 U.S.C. §112.

The sequence of the polynucleotides contained in the deposited material, as well as the amino acid sequence of the polypeptide encoded thereby, are controlling in the event of any conflict with any description of sequences herein.

A license may be required to make, use or sell the deposited materials, and no such license is hereby granted.

Polypeptides

The present invention further relates to a human NKAF II polypeptide which has the deduced amino acid sequence of FIG. 1 (SEQ ID NO:2).

The invention also relates to fragments, analogs and derivatives of these polypeptides.

The terms "fragment," "derivative" and "analog" when referring to the polypeptide of FIG. 1 (SEQ ID NO:2) means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide. In certain preferred embodiments it is a recombinant polypeptide.

The fragment, derivative or analog of the polypeptide of FIG. 1 (SEQ ID NO:2) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among the particularly preferred embodiments of the invention in this regard are polypeptides having the amino acid sequence of NKAF II set out in FIG. 1 (SEQ ID NO:2), variants, analogs, derivatives and fragments thereof, and variants, analogs and derivatives of the fragments. Alternatively, particularly preferred embodiments of the invention in this regard are polypeptides having the amino acid sequence of the NKAF II of the cDNA in the deposited clone, variants, analogs, derivatives and fragments thereof, and variants, analogs and derivatives of the fragments.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Further particularly preferred in this regard are variants, analogs, derivatives and fragments, and variants, analogs and derivatives of the fragments, having the amino acid sequence of the NKAF II polypeptide of FIG. 1 (SEQ ID NO:2) in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the NKAF II. Also especially preferred in this regard are conservative substitutions. Most highly preferred are polypeptides having the amino acid sequence of FIG. 1 (SEQ ID NO:2) without substitutions.

The polypeptides and polynucleotides of the present invention are preferably provided in an isolated form, and preferably are purified to homogeneity.

The polypeptides of the present invention also include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides.

Fragments or portions of the polynucleotides of the present invention may be used to synthesize full-length polynucleotides of the present invention.

Fragments

Also among preferred embodiments of this aspect of the present invention are polypeptides comprising fragments of NKAF II, most particularly fragments of the NKAF II having the amino acid set out in FIG. 1 (SEQ ID NO:2), and fragments of variants and derivatives of the NKAF II of FIG. 1 (SEQ ID NO:2).

In this regard a fragment is a polypeptide having an amino acid sequence that entirely is the same as part but not all of the amino acid sequence of the aforementioned NKAF II polypeptides and variants or derivatives thereof.

Such fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a NKAF II polypeptide of the present comprised within a precursor polypeptide designed for expression in a host and having heterologous pre and pro-polypeptide regions fused to the amino terminus of the NKAF II fragment and an additional region fused to the carboxyl terminus of the fragment. Therefore, fragments in one aspect of the meaning intended herein, refers to the portion or portions of a fusion polypeptide or fusion protein derived from NKAF II.

As representative examples of polypeptide fragments of the invention, there may be mentioned those which have from about 21 to about 225 amino acids.

In this context about includes the particularly recited range and ranges larger or smaller by several, a few, 5, 4, 3, 2 or 1 amino acid at either extreme or at both extremes. For instance, about 225 amino acids in this context means a polypeptide fragment of 225 plus or minus several, a few, 5, 4, 3, 2 or 1 amino acids to 225 plus or minus several a few, 5, 4, 3, 2 or 1 amino acid residues, i.e., ranges as broad as 21 minus several amino acids to 225 plus several amino acids to as narrow as 21 plus several amino acids to 225 minus several amino acids.

Highly preferred in this regard are the recited ranges plus or minus as many as 5 amino acids at either or at both extremes. Particularly highly preferred are the recited ranges plus or minus as many as 3 amino acids at either or at both the recited extremes. Especially particularly highly preferred are ranges plus or minus 1 amino acid at either or at both extremes or the recited ranges with no additions or deletions. Most highly preferred of all in this regard are fragments from about 21 to about 225 amino acids.

Among especially preferred fragments of the invention are truncation mutants of NKAF II. Truncation mutants include NKAF II polypeptides having the amino acid sequence of FIG. 1 (SEQ ID NO:2), or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out about also are preferred embodiments of truncation fragments, which are especially preferred among fragments generally.

Also preferred in this aspect of the invention are fragments characterized by structural or functional attributes of NKAF II. Preferred embodiments of the invention in this regard include fragments that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of NKAF II.

Certain preferred regions in these regards include, but are not limited to, regions of the aforementioned types identified by analysis of the amino acid sequence set out in FIG. 1 (SEQ ID NO:2). Such preferred regions include Garnier-Robson alpha-regions, beta-regions, turn-regions and coil-regions, Chou-Fasman alpha-regions, beta-regions and turn-regions, Kyte-Doolittle hydrophilic regions and hydrophilic regions, Eisenberg alpha and beta amphipathic regions, Karplus-Schulz flexible regions, Emini surface-forming regions and Jameson-Wolf high antigenic index regions.

Among highly preferred fragments in this regard are those that comprise regions of NKAF II that combine several structural features, such as several of the features set out above. In this regard, the regions defined by the residues about 19 to 225, 20 to 225 and 21 to 225 of FIG. 1 (2 to 208, 3 to 208, and 4 to 208 in SEQ ID NO:2, respectively), which all are characterized by amino acid compositions highly characteristic of turn-regions, hydrophilic regions, flexible-regions, surface-forming regions, and high antigenic index-regions, are especially highly preferred regions. Such regions may be comprised within a larger polypeptide or may be by themselves a preferred fragment of the present invention, as discussed above. It will be appreciated that the term "about" as used in this paragraph has the meaning set out above regarding fragments in general.

Further preferred regions are those that mediate activities of NKAF II. Most highly preferred in this regard are fragments that have a chemical, biological or other activity of NKAF II, including those with a similar activity or an improved activity, or with a decreased undesirable activity. Highly preferred in this regard are fragments that contain regions that are homologs in sequence, or in position, or in both sequence and to active regions of related polypeptides, such as the related polypeptides set out in FIG. 2 (SEQ ID NO:11), which include human eosinophil granule major basic protein. Among particularlypreferred fragments in these regards are truncation mutants, as discussed above.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspondent to the preferred fragments, as discussed above.

Vectors, Host Cells and Expression

The present invention also relates to vectors which include polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. For instance, polynucleotides may be introduced into host cells using well known techniques of infection, transduction, transfection, transvection and transformation. The polynucleotides may be introduced alone or with other polynucleotides. Such other polynucleotides may be introduced independently, co-introduced or introduced joined to the polynucleotidesofthe invention.

Thus, for instance, polynucleotides of the invention may be transfected into host cells with another, separate, polynucleotide encoding a selectable marker, using standard techniques for co-transfection and selection in, for instance, mammalian cells. In this case the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation also may be used to introduce polynucleotides into a host. If the vector is a virus, it may be packaged in vitro or introduced into a packaging cell and the packaged virus may be transduced into cells. A wide variety of techniques suitable for making polynucleotidesand for introducing polynucleotides into cells in accordance with this aspect of the invention are well known and routine to those of skill in the art. Such techniques are reviewed at length in Sambrook et al. cited above, which is illustrative of the many laboratory manuals that detail these techniques.

In accordance with this aspect of the invention the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. The vectors, in the case of phage and viral vectors also may be and preferably are introduced into cells as packaged or encapsidated virus by well known techniques for infection and transduction. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression generally will be suitable for expression of polypeptides of the present invention as will be apparent to those of skill in the art.

A great variety of expression vectors can be used to express a polypeptide of the invention. Such vectors include chromosomal, episomal and virus-derived vectors e.g., vectors derived from bacterial plasmids, from bacteriophage, from yeast episomes, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those skill, are set forth in great detail in Sambrook et al. cited elsewhere herein.

The DNA sequence in the expression vector is operatively linked to appropriate expression control sequence(s), including, for instance, a promoter to direct mRNA transcription. Representatives of such promoters include the phage lambda PL promoter, the E. coli lac, trp and tac promoters, the SV40 early and late promoters and promoters of retroviral LTRs, to name just a few of the well-known promoters. It will be understood that numerous promoters not mentioned are suitable for use in this aspect of the invention are well known and readily may be employed by those of skill in the manner illustrated by the discussion and the examples herein.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline, theomycin, kanamycin or ampicillin resistance genes for culturing *E. coli* and other bacteria.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as *E. coli*, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Hosts for of a great variety of expression constructs are well known, and those of skill will be enabled by the present disclosure readily to select a host for expressing a polypeptides in accordance with this aspect of the present invention.

Various mammalian cell culture systems can be employed for expression, as well. Examples of mammalian expression systems include the COS-7 lines of monkey kidney fibroblast, described in Gluzman et al., Cell 23: 175 (1981). Other cell lines capable of expressing a compatible vector include for example, the C127, 3T3, CHO, HeLa, human kidney 293 and BHK cell lines.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH 1 6a, pNH 1 8A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("cat") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available. Two such vectors are pKK232-8 and pCM7. Thus, promoters for expression of polynucleotides of the present invention include not only well known and readily available promoters, but also promoters that readily may be obtained by the foregoing technique, using a reporter gene.

Among known bacterial promoters suitable for expression of polynucleotides and polypeptides in accordance with the present invention are the *E. coli* lacI and lacZ promoters, the T3 and T7 promoters, the T5 tac promoter, the lambda PR, PL promoters and the trp promoter. Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Selection of appropriate vectors and promoters for expression in a host cell is a well known procedure and the requisite techniques for expression vector construction, introduction of the vector into the host and expression in the host are routine skills in the art.

Generally, recombinant expression vectors will include origins of replication, a promoter derived from a highly-expressed gene to direct transcription of a downstream structural sequence, and a selectable marker to permit isolation of vector containing cells after exposure to the vector.

The present invention also relates to host cells containing the above-described constructs discussed above. The host cell can be a higher eukaryotic cell, such as a mammalian cell, or a lower eukaryotic cell, such as a yeast cell, or the host cell can be a prokaryotic cell, such as a bacterial cell.

Constructs in host cells can be used in a conventional manner to produce the gene product encoded by the recombinant sequence. Alternatively, the polypeptides of the invention can be syntheticallyproduced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., MOLECULAR CLONING: A LABORATORY MANUAL, 2nd Ed., Cold Spring Harbor Laboratory Press, Cold Spring Harbor, N.Y. (1989).

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiating AUG. Also, generally, there will be a translation stop codon at the end of the polypeptide and there will be a polyadenylation signal and a transcription termination signal appropriately disposed at the 3' end of the transcribed region.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, region also may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

Following transformation of a suitable host strain and growth of the host strain to an appropriate cell density, where the selected promoter is inducible it is induced by appropriate means (e.g., temperature shift or exposure to chemical inducer) and cells are cultured for an additional period.

Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

The NKAF II polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and or purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

NKAF II polynucleotides and polypeptides may be used in accordance with the present invention for a variety of applications, particularly those that make use of the chemical and biological properties of NKAF II. Among these are applications in prevention of neoplasia. Additional applications relate to diagnosis and to treatment of disorders of cells, tissues and organisms. These aspects of the invention are illustrated further by the following discussion.

Polynucleotide Assays

This invention is also related to the use of the NKAF II polynucleotides to detect complementary polynucleotides such as, for example, as a diagnostic reagent. Detection of a mutated form of NKAF II associated with a dysfunction will provide a diagnostic tool that can add or define a diagnosis of a disease or susceptibility to a disease which results from under-expression over-expressionor altered expression of NKAF II, such as, for example, eosinophilia or bronchial asthma.

Individuals carrying mutations in the human NKAF II gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR prior to analysis. PCR (Saiki et al., Nature, 324: 163–166 (1986)). RNA or cDNA may also be used in the same ways. As an example, PCR primers complementary to the nucleic acid encoding NKAF II can be used to identify and analyze NKAF II expression and mutations. For example, deletions and insertions can be detected by a change in size of the amplified product in comparison to the normal genotype. Point mutations can be identified by hybridizing amplified DNA to radiolabeled NKAF II RNA or alternatively, radiolabeled NKAF II antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230: 1242 (1985)).

Sequence changes at specific locations also may be revealed by nuclease protection assays, such as RNase and S1 protection or the chemical cleavage method (e.g., Cotton et al., Proc. Natl. Acad. Sci., USA, 85: 4397–4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In addition to more conventional gel-electrophoresis and DNA sequencing, mutations also can be detected by in situ analysis.

Chromosome Assays

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a NKAF II gene. This can be accomplished using a variety of well known techniques and libraries, which generally are available commercially. The genomic DNA the is used for in situ chromosome mapping using well known techniques for this purpose. Typically, in accordance with routine procedures for chromosome mapping, some trial and error may be necessary to identify a genomic probe that gives a good in situ hybridization signal.

In some cases, in addition, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with cDNA as short as 50 or 60 bases. For a review of this technique, see Verma et al., HUMAN CHROMOSOMES: A MANUAL OF BASIC TECHNIQUES, Pergamon Press, New York (1988).

Once a sequence has been mapped to a precise chromosomal location, the physical position of the sequence on the chromosome can be correlated with genetic map data. Such data are found, for example, in V. McKusick, MENDELIAN INHERITANCE IN MAN, available on line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Polypeptide Assays

The present invention also relates to a diagnostic assays such as quantitative and diagnostic assays for detecting levels of NKAF II protein in cells and tissues, including determination of normal and abnormal levels. Thus, for instance, a diagnostic assay in accordance with the invention for detecting over-expression of NKAF II protein compared to normal control tissue samples may be used to detect the presence of eosinophilia, for example. Assay techniques that can be used to determine levels of a protein, such as an NKAF II protein of the present invention, in a sample derived from a host are well-known to those of skill in the art. Such assay methods include radioimmunoassays, competitive-bindingassays, Western Blot analysis and ELISA assays. Among these ELISAs frequently are preferred. An ELISA assay initially comprises preparing an antibody specific to NKAF II, preferably a monoclonal antibody. In addition a reporter antibody generally is prepared which binds to the monoclonal antibody. The reporter antibody is attached a detectable reagent such as radioactive, fluorescent or enzymatic reagent, in this example horseradish peroxidase enzyme.

To carry out an ELISA a sample is removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any NKAF II proteins attached to the polystyrene dish. Unbound monoclonal antibody is washed out with buffer. The reporter antibody linked to horseradish peroxidase is placed in the dish resulting in binding of the reporter antibody to any monoclonal antibody bound to NKAF II. Unattached reporter antibody is then washed out. Reagents for peroxidase activity, including a colorimetric substrate are then added to the dish. Immobilized peroxidase, linked to NKAF II through the primary and secondary antibodies, produces a colored reaction product. The amount of color developed in a given time period indicates the amount of NKAF II protein present in the sample. Quantitative results typically are obtained by reference to a standard curve.

A competition assay may be employed wherein antibodies specific to NKAF II attached to a solid support and labeled NKAF II and a sample derived from the host are passed over the solid support and the amount of label detected attached to the solid support can be correlated to a quantity of NKAF II in the sample.

Antibodies

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler, G. and Milstein, C., Nature 256: 495–497 (1975), the trioma technique, the human B-cell hybridoma technique (Kozbor et al., Immunology Today 4: 72 (1983) and the EBV-hybridoma technique to produce human monoclonal antibodies (Cole et al., pg. 77–96 in MONOCLONAL ANTIBODIES AND CANCER THERAPY, Alan R. Liss, Inc. (1985).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

The above-described antibodies may be employed to isolate or to identify clones expressing the polypeptide or purify the polypeptide of the present invention by attachment of the antibody to a solid support for isolation and/or purification by affinity chromatography.

Thus, among others, NKAF II may be employed to inhibit the growth of certain tumor cell lines, and other neoplasias due to the cytotoxic effect of NKAF II.

The polypeptide of the present invention may also be employed to prevent inflammation, to treat parasitic infection due to its cytotoxic effect on certain parasites, to augment the effects of natural killer protein to treat neoplasias such as tumors and cancers, to prevent inflammation, to treat parasitic infection, to regulate hemaetopoesis, to prevent damage from superoxide radicals in the body, for example, to prevent tissue injury and aging and to enhance an immunological response.

NKAF II Binding Molecules and Assays

This invention also provides a method for identification of molecules, such as receptor molecules, that bind NKAF II. Genes encoding proteins that bind NKAF II, such as receptor proteins, can be identified by numerous methods known to those of skill in the art, for example, ligand panning and FACS sorting. Such methods are described in many laboratory manuals such as, for instance, Coligan et al., Current Protocols in Immunology 1(2): Chapter 5 (199 1).

For instance, expression cloning may be employed for this purpose. To this end polyadenylated RNA is prepared from a cell responsive to NKAF II, a cDNA library is created from this RNA, the library is divided into pools and the pools are transfected individually into cells that are not responsive to NKAF II. The transfected cells then are exposed to labeled NKAF II. (NKAF II can be labeled by a variety of well-known techniques including standard methods of radio-iodinationor inclusion of a recognition site for a site-specific protein kinase.) Following exposure, the cells are fixed and binding of NKAF II is determined. These procedures conveniently are carried out on glass slides.

Pools are identified of cDNA that produced NKAF II-binding cells. Sub-pools are prepared from these positives, transfected into host cells and screened as described above. Using an iterative sub-pooling and re-screening process, plasmids containing one or more single clones that encode the putative binding molecule, such as a receptor molecule, can be isolated and the clones are sequenced.

Alternatively a labeled ligand can be photoaffinity linked to a cell extract, such as a membrane or a membrane extract, prepared from cells that express a molecule that it binds, such as a receptor molecule. Cross-linked material is resolved by polyacrylamide gel electrophoresis ("PAGF") and exposed to X-ray film. The labeled complex containing the ligand-receptor can be excised, resolved into peptide fragments, and subjected to protein microsequencing. The amino acid sequence obtained from microsequencing can be used to design unique or degenerate oligonucleotide probes to screen cDNA libraries to identify genes encoding the putative receptor molecule.

Polypeptides of the invention also can be used to assess NKAF II binding capacity of NKAF II binding molecules, such as receptor molecules, in cells or in cell-free preparations.

Agonists and Antagonists—Assays and Molecules

The invention also provides a method of screening compounds to identify those which enhance or block the action of NKAF II on cells, such as its interaction with NKAF II-binding molecules such as receptor molecules. An agonist is a compound which increases the natural biological functions of NKAF II or which functions in a manner similar to NKAF II, while antagonists decrease or eliminate such functions.

For example, a cellular compartment, such as a membrane or a preparation thereof, such as a membrane-preparation, may be prepared from a cell that expresses a molecule that binds NKAF II, such as a molecule of a signaling or regulatory pathway modulated by NKAF II. The preparation is incubated with labeled NKAF II in the absence or the presence of a candidate molecule which may be a NKAF II agonist or antagonist. The ability of the candidate molecule to bind the binding molecule is reflected in decreased binding of the labeled ligand. Molecules which bind gratuitously, i.e., without inducing the effects of NKAF II on binding the NKAF II binding molecule, are most likely to be good antagonists. Molecules that bind well and elicit effects that are the same as or closely related to NKAF II, are good agonists.

NKAF II-like effects of potential agonists and antagonists may by measured, for instance, by determining activity of a second messenger system following interaction of the candidate molecule with a cell or appropriate cell preparation, and comparing the effect with that of NKAF II or molecules that elicit the same effects as NKAF II. Second messenger systems that may be useful in this regard include but are not limited to AMP guanylate cyclase, ion channel or phosphoinositide hydrolysis second messenger systems.

Another example of an assay for NKAF II antagonists is a competitive assay that combines NKAF II and a potential antagonist with membrane-bound NKAF II receptor molecules or recombinant NKAF II receptor molecules under appropriate conditions for a competitive inhibition assay. NKAF II can be labeled, such as by radioactivity, such that the number of NKAF II molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing NKAF II-induced activities, thereby preventing the action of NKAF II by excluding NKAF II from binding.

Other potential antagonists include antisense molecules. Antisense technology can be used to control gene expression through antisense DNA or RNA or through triple-helix formation. Antisense techniques are discussed, for example, in—Okano, J. Neurochem. 56: 560 (1991); OLIGODEOXYNUCLEOTIDES AS ANTISENSE INHIBITORS OF GENE EXPRESSION, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene (or promotor) involved in transcription thereby preventing transcription and the production of NKAF II. The antisense RNA oligonucleotide hybridizes to the mRNA in vivo and blocks translation of the mRNA molecule into NKAF II polypeptide. The oligonucleotides described above can also be delivered to cells such that the antisense RNA or DNA may be expressed in vivo to inhibit production of NKAF II.

The antagonists may be employed in a composition with a pharmaceutically acceptable carrier, e.g., as hereinafter described.

The antagonists may be employed for instance to treat and/or prevent the action of such polypeptide, for example, to prevent allergic inflammation, hypersensitivity, bronchial asthma, eosinophilia, chronic urticaria, atopic dermatitis, Kimura's disease, and bone marrow transplants rejection.

Compositions

The invention also relates to compositions comprising the polynucleotide or the polypeptides discussed above or the agonists or antagonists. Thus, the polypeptides of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

Kits

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Administration

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 mg/kg body weight. In most cases they will be administered in an amount not in excess of about 8 mg/kg body weight per day. Preferably, in most cases, dose is from about 10 mg/kg to about 1 mg/kg body weight, daily. It will be appreciated that optimum dosage will be determined by standard methods for each treatment modality and indication, taking into account the indication, its severity, route of administration, complicating conditions and the like.

Gene Therapy

The NKAF II polynucleotides, polypeptides, agonists and antagonists that are polypeptides may be employed in accordance with the present invention by expression of such polypeptides in vivo, in treatment modalities often referred to as "gene therapy."

Thus, for example, cells from a patient may be engineered with a polynucleotide, such as a DNA or RNA, encoding a polypeptide ex vivo, and the engineered cells then can be provided to a patient to be treated with the polypeptide. For example, cells may be engineered ex vivo by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector, as discussed above. The retroviral expression construct then may be isolated and introduced into a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors herein above mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

Such vectors well include one or more promoters for expressing the polypeptide. Suitable promoters which may be employed include, but are not limited to, the retroviral LTR; the SV40 promoter; and the human cytomegalovirus (CMV) promoter described in Miller et al., Biotechniques 7: 980–990 (1989), or any other promoter (e.g., cellular promoters such as eukaryotic cellular promoters including, but not limited to, the histone, RNA polymerase III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention will be placed under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoA1 promoter; human globin promoters; viral thymidine kinase promoters, such as the Herpes Simplex thymidine kinase promoter; retroviral LTRs (including the modified retroviral LTRs herein above described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Y-2, Y-AM, PA12, T19-14X, VT-19-17-H2, YCRE, YCRIP GP+E-86, GP+envAm12, and DAN cell lines as described in Miller, A., Human Gene Therapy 1: 5–14 (1990). The vector may be transduced into the packaging cells through any means known in the art. Such means include, but are not limited to, electroporation, the use of liposomes, and CaPO4 precipitation. In one alternative, the retroviral plasmid vector may be encapsulated into a liposome, or coupled to a lipid, and then administeredto a host.

The producer cell line will generate infectious retroviral vector particles, which include the nucleic acid sequence(s) encoding the polypeptides. Such retroviral vector particles then may be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

EXAMPLES

The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

Certain terms used herein are explained in the foregoing glossary.

All examples were carried out using standard techniques, which are well known and routine to those of skill in the art, except where otherwise described in detail. Routine molecular biology techniques of the following examples can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989), herein referred to as "Sambrook."

All parts or amounts set out in the following examples are by weight, unless otherwise specified.

Unless otherwise stated size separation of fragments in the examples below was carried out using standard techniques of agarose and polyacrylamide gel electrophoresis ("PAGE") in Sambrook and numerous other references such as, for instance, by Goeddel et al., Nucleic Acids Res. 8: 4057 (1980).

Unless described otherwise, ligations were accomplished using standard buffers, incubation temperatures and times, approximately equimolar amounts of the DNA fragments to be ligated and approximately 10 units of T4 DNA ligase ("ligase") per 0.5 mg of DNA.

Example 1

Expression and Purification of Mature Human NKAF II Using Bacteria

The DNA sequence encoding human NKAF II in the deposited polynucleotide was amplified using PCR oligonucleotide primers specific to the amino acid carboxyl terminal sequence of the human NKAF II protein and to vector sequences 3' to the gene. Additional nucleotides containing restriction sites to facilitate cloning were added to the 5' and 3' sequences respectively.

The 5' oligonucleotide primer had the sequence 5' CGC <u>CCATGG</u> AGA ATG ATG CCC CCC AT 3' (SEQ ID NO:3) containing the underlined Nco I restriction site, which encodes a start AUG, followed by 17 nucleotides of the human NKAF II coding sequence set out in FIG. 1 (SEQ ID NO:1) beginning with the first base of the first mature codon as predicted by the computer program PSORT. The molecule encodes a particularly preferred fragment of the mature NKAF II polypeptide having the amino acid sequence shown as amino acid residues 3 to 208 in SEQ ID NO:2.

The 3' primer had the sequence 5' CGC <u>AAGCTT</u> CTC CGT GCC GCT GGC TTA 3' (SEQ ID NO:4) containing the underlined Hind III restriction site followed by nucleotides complementary to the last 18 NKAF II non-coding sequence next to stop codon set out in FIG. 1 (SEQ ID NO:1), including the stop codon.

The restrictions sites were convenient to restriction enzyme sites in the bacterial expression vectors pQE-60, which were used for bacterial expression in these examples. (Qiagen, Inc. Chatsworth, Calif.). pQE-60 encodes ampicillin antibiotic resistance ("Ampr") and contains a bacterial origin of replication ("ori"), an IPTG inducible promoter, a ribosome binding site ("RBS"), a 6-His tag and restriction enzyme sites.

The amplified human NKAF II DNA and the vector pQE-60 both were digested with Nco I and Hind III and the digested DNAs then were ligated together. Insertion of the NKAF II DNA into the restricted vector placed the NKAF II coding region downstream of and operably linked to the vector's IPTG-inducible promoter and in-frame with an initiating AUG appropriately positioned for translation of NKAF II.

The ligation mixture was transformed into competent *E. coli* cells using standard procedures. Such procedures are described in Sambrook et al., MOLECULAR CLONING: A LABORATORY MANUAL, 2nd Ed.; Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kanr"), was used in carrying out the illustrative example described here. This strain, which is only one of many that are suitable for expressing NKAF II, is available commercially from Qiagen.

Transformants were identified by their ability to grow on LB plates in the presence of ampicillin. Plasmid DNA was isolated from resistant colonies and the identity of the cloned DNA was confirmed by restriction analysis.

Clones containing the desired constructs were grown overnight ("O/N") in liquid culture in LB media supplemented with both ampicillin (100 ug/ml) and kanamycin (25 ug/ml).

The O/N culture was used to inoculate a large culture, at a dilution of approximately 1:100 to 1:250. The cells were grown to an optical density at 600nm ("OD600") of between 0.4 and 0.6. Isopropyl-B-D-thiogalactopyranoside ("IPTG") was then added to a final concentration of 1 mM to induce transcription from lac repressor sensitive promoters, by inactivating the lacI repressor. Cells subsequently were incubated further for 3 to 4 hours. Cells then were harvested by centrifugation and disrupted, by standard methods. Inclusion bodies were purified from the disrupted cells using routine collection techniques, and protein was solubilized from the inclusion bodies into 8M urea. The 8M urea solution containing the solubilizedprotein was passed over a PD-10 column in 2×phosphate buffered saline ("PBS"), thereby removing the urea, exchanging the buffer and refolding the protein. The protein was purified by a further step of chromatography to remove endotoxin. Then, it was sterile filtered. The sterile filtered protein preparation was stored in 2×PBS at a concentration of 95 micrograms per mL.

Analysis of the preparation by standard methods of polyacrylamide gel electrophoresis revealed that the preparation contained about 95% monomer NKAF II having the expected molecular weight of, approximately, 23.3 kDa.

Example 2

Cloning and Expression of Human NKAF II in a Baculovirus Expression System

The cDNA sequence encoding the full length human NKAF II protein, in the deposited clone is amplified using PCR oligonucleotide primers corresponding to the 5' and 3' sequences of the gene:

The 5' primer has the sequence 5' CGC GGATCC GCC ATC ATG CAA CGC CTC TTG 3' (SEQ ID NO:5) containing the underlined Bam HI restriction enzyme site followed by bases of the sequence of NKAF II of FIG. 1 (SEQ ID NO:1). Inserted into an expression vector, as described below, the 5' end of the amplified fragment encoding human NKAF II provides an efficient signal peptide. An efficient signal for initiation of translation in eukaryotic cells, as described by Kozak, M., J. Mol. Biol. 196: 947–950 (1987) is appropriately located in the vector portion of the construct.

The 3' primer has the sequence 5' CGC GGT ACC CTC CGT GCC GCT GGC TTA 3' (SEQ ID NO:6) containing the underlined Asp718 restriction followed by nucleotides complementary to 18 nucleotides of NKAF II non-coding sequence next to stop codon.

The amplified fragment is isolated from a 1% agarose gel using a commercially available kit ("Geneclean," BIO 101 Inc., La Jolla, Calif.). The fragment then is digested with BamH1 and Asp718 and again is purified on a 1% agarose gel. This fragment is designated herein F2.

The vector pA2 is used to express the NKAF II protein in the baculovirus expression system, using standard methods, such as those described in Summers et al, A MANUAL OF METHODS FOR BACULOVIRUS VECTORS AND INSECT CELL CULTURE PROCEDURES, Texas Agricultural Experimental Station Bulletin No. 1555 (1987). This expression vector contains the strong polyhedrin promoter of the Autographa califomica nuclear polyhedrosis virus (AcMNPV) followed by convenient restriction sites. The signal peptide of AcMNPV gp67, including the N-terminal methionine, is locatedjust upstream of a BamH1 site. The polyadenylation site of the simian virus 40 ("SV40") is used for efficient polyadenylation. For an easy selection of recombinant virus the beta-galactosidasegene from *E.coli* is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of pA2, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., Virology 170: 31–39, among others.

The plasmid is digested with the restriction enzymes and Bam HI and Asp718 and then is dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V2".

Fragment F2 and the dephosphorylated plasmid V2 are ligated together with T4 DNA ligase. *E. coli* HB101 cells are transformed with ligation mix and spread on culture plates. Bacteria are identified that contain the plasmid with the human NKAF II gene by digesting DNA from individual colonies using Bam HI and Asp718 and then analyzing the digestion product by gel electrophoresis. The sequence of the cloned fragment is confirmed by DNA sequencing. This plasmid is designated herein pBacNKAF II.

5 mg of the plasmid pBacNKAF II is co-transfected with 1.0 mg of a commercially available linearized baculovirus DNA ("BaculoGoldÔ baculovirus DNA", Pharmingen, San Diego, Calif.), using the lipofection method described by Felgner et al., Proc. Natl. Acad. Sci. USA 84: 7413–7417 (1987). 1 mg of BaculoGoldÔ virus DNA and 5 mg of the plasmid pBacNKAF II are mixed in a sterile well of a microtiter plate containing 50 ml of serum free Grace's medium (Life Technologies Inc., Gaithersburg, Md.). Afterwards 10 ml Lipofectin plus 90 ml Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, cited above. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10).

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 ml of Grace's medium. The agar is removed by a brief centrifugation and the supernatant containing the recombinant baculovirus is used to infect Sf9 cells seeded in 35 mm dishes. Four days later the supernatants of these culture dishes are harvested and then they are stored at 4° C. A clone containing properly inserted NKAF II is identified by DNA analysis including restriction mapping and sequencing. This is designated herein as V-NKAF II.

Sf9 cells are grown in Grace's medium supplemented with 10% heat-inactivated FBS. The cells are infected with the recombinant baculovirus V-NKAF II at a multiplicity of infection ("MOI") of about 2 (about 1 to about 3). Six hours later the medium is removed and is replaced with SF900 II medium minus methionine and cysteine (available from Life Technologies Inc., Gaithersburg). 42 hours later, 5 mCi of 35S-methionine and 5 mCi 35S cysteine (available from Amersham) are added. The cells are further incubated for 16 hours and then they are harvested by centrifugation, lysed and the labeled proteins are visualized by SDS-PAGE and autoradiography.

The N-terminal sequence of the NKAF II polypeptide produced according to the above method was determined to begin with the amino acid residue 1 as shown in SEQ ID NO:2.

Example 3

Expression of NKAF II in COS Cells

The expression plasmid, NKAF II HA, is made by cloning a cDNA encoding NKAF II into the expression vector pcDNAI/Amp (which can be obtained from Invitrogen, Inc.).

The expression vector pcDNAI/amp contains: (1) an E.coli origin of replication effective for propagation in E. coli and other prokaryotic cell; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker.

A DNA fragment encoding the entire NKAF II precursor and a HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., Cell 37: 767 (1984). The fusion of the HA tag to the target protein allows easy detection of the recombinant protein with an antibody that recognizes the HA epitope.

The plasmid construction strategy is as follows.

The NKAF II cDNA of the deposit clone is amplified using primers that contained convenient restriction sites, much as described above regarding the construction of expression vectors for expression of NKAF II in E. coli and S. furgiperda.

To facilitate detection, purification and characterization of the expressed NKAF II, one of the primers contains a heamaglutinin tag ("HA tag") as described above.

Suitable primers include that following, which are used in this example.

The 5' primer 5' CGC GGATCC GCC ATC ATG CAA CGC CTC TTG 3' (SEQ ID NO:7) contains the underlined Bam HI site, an AUG start codon and 15 codons thereafter.

The 3' primer, containing the underlined Xba I site; 15 bp of 3' coding sequence (at the 3' end); and hemagluttinin tag has the following sequence, 5' CGC TCT AGA TCA AGC GTA GTC TGG GAC GTC GTA TGG GTA GAA GGA GCA GAC GAA 3' (SEQ ID NO:8).

The PCR amplified DNA fragment and the vector, pcDNAI/Amp, are digested with and then ligated. The ligation mixture is transformed into E. coli strain SURE (available from Stratagene Cloning Systems, 11099 North Torrey Pines Road, La Jolla, Calif. 92037) the transformed culture is plated on ampicillin media plates which then are incubated to allow growth of ampicillin resistant colonies. Plasmid DNA is isolated from resistant colonies and examined by restriction analysis and gel sizing for the presence of the NKAF II-encoding fragment.

For expression of recombinant NKAF II, COS cells are transfected with an expression vector, as described above, using DEAE-DEXTRAN, as described, for instance, in Sambrook et al., MOLECULAR CLONING: A LABORATORY MANUAL, Cold Spring Laboratory Press, Cold Spring Harbor, N.Y. (1989).

Cells a re incubated under cond itions for expression of NKAF II by the vector.

Expression of the NKAF II HA fusion protein is detected by radiolabelling and immunoprecipitation, using methods described in, for example Harlow et al., ANTIBODIES: A LABORATORY MANUAL, 2nd Ed.; Cold Spring Harbor Laboratory Press, Cold Spring Harbor, N.Y. (1988). To this end, two days after transfection, the cells are labeled by incubation in media containing 35S-cysteine for 8 hours. The cells and the media are collected, and the cells are washed and the lysed with detergent-containing RIPA buffer: 150 mM NaCl, 1% NP-40, 0.1% SDS, 1% NP-40,0.5% DOC, 50 mM TRIS, pH 7.5, as describedby Wilson et al. cited above. Proteins are precipitat ed from the cell lysate and from the culture media using an HA-specific monoclonal antibody. The precipitated proteins then are analyzed by SDS-PAGE gels and autoradiography. An expression product of the expect ed size is seen in the cell lysate, which is not seen in negative controls.

Example 4

Tissue Distribution of NKAF II Expression

Northern blot analysis is carried out to examine the levels of expression of NKAF II in human tissues, using methods described by, among others, Sambrook et al, cited above. Total cellular RNA samples are isolated with RNAzolÔ B system (Biotecx Laboratories, Inc. 6023 South Loop East, Houston, Tex. 77033).

About 10 mg of Total RNA is isolated from tissue samples. The RNA is size resolved by electrophoresis through a 1% agarose gel under strongly denaturing conditions. RNA is blotted from the gel onto a nylon filter, and the filter then is prepared for hybridization to a detectably labeled polynucleotide probe.

As a probe to detect mRNA that encodes NKAF II, the antisense strand of the coding region of the cDNA insert in the deposited clone is labeled to a high specific activity. The cDNA is labeled by primer extension, using the Prime-It kit, available from Stratagene. The reaction is carried out using 50 ng of the cDNA, following the standard reaction protocol as recommended by the supplier. The labeled polynucleotide is purified away from other labeled reaction components by column chromatography using a Select-G-50 column, obtained from 5-Prime—3-Prime, Inc. of 5603 Arapahoe Road, Boulder, Col. 80303.

The labeled probe is hybridized to the filter, at a concentration of 1,000,000 cpm/ml, in a small volume of 7% SDS, 0.5 M NaPO4, pH 7.4 at 65° C., overnight.

Thereafter the probe solution is drained and the filter is washed twice at room temperature and twice at 60° C. with 0.5×SSC, 0.1% SDS. The filter then is dried and exposed to film at −70° C. overnight with an intensifying screen.

Autoradiography shows that mRNA for NKAF II is abundant in fetal liver and bone marrow.

Example 5

Gene Therapeutic Expression of Human NKAF II

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted—the chunks of tissue remain fixed to the bottom of the flask—and fresh media is added (e.g., Ham's F12 media, with 10% FBS, penicillin and streptomycin). The tissue is then incubated at 37° C. for approximately one week. At this time, fresh media is added and subsequently changed every several days. After an additional two weeks in culture, a monolayer of fibroblasts emerges. The monolayer is trypsinized and scaled into larger flasks.

A vector for gene therapy is digested with restriction enzymes for cloning a fragment to be expressed. The digested vector is treated with calf intestinal phosphatase to prevent self-ligation. The dephosphorylated, linear vector is fractionated on an agarose gel and purified.

NKAF II cDNA capable of expressing active NKAF II, is isolated. The ends of the fragment are modified, if necessary, for cloning into the vector. For instance, 5' overhanging may be treated with DNA polymerase to create blunt ends. 3' overhanging ends may be removed using S1 nuclease. Linkers may be ligated to blunt ends with T4 DNA ligase.

Equal quantities of the Moloney murine leukemia virus linear backbone and the NKAF II fragment are mixed together and joined using T4 DNA ligase. The ligation mixture is used to transform E. Coli and the bacteria are then plated onto agar-containing kanamycin. Kananycin pheno-type and restriction analysis confirm that the vector has the properly inserted gene.

Packaging cells are grown in tissue culture to confluent density in Dulbecco's Modified Eagles Medium (DMEM) with 10% calf serum (CS), penicillin and streptomycin. The vector containing the NKAF II gene is introduced into the packaging cells by standard techniques. Infectious viral particles containing the NKAF II gene are collected from the packaging cells, which now are called producer cells.

Fresh media is added to the producer cells, and after an appropriate incubation period media is harvested from the plates of confluent producer cells. The media, containing the infectious viral particles, is filtered through a Millipore filter to remove detached producer cells. The filtered media then is used to infect fibroblast cells. Media is removed from a sub-confluent plate of fibroblasts and quickly replaced with the filtered media. Polybrene (Aldrich) may be included in the media to facilitate transduction. After appropriate incubation, the media is removed and replaced with fresh media. If the titer of virus is high, then virtually all fibroblasts will be infected and no selection is required. If the titer is low, then it is necessary to use a retroviral vector that has a selectable marker, such as neo or his, to select out transduced cells for expansion.

Engineered fibroblasts then may be injected into rats, either alone or after having been grown to confluence on microcarrier beads, such as cytodex 3 beads. The injected fibroblasts produce NKAF II product, and the biological actions of the protein are conveyed to the host.

Example 6

Expression of Recombinant NKAF II in CHO Cells

The vector pC1 is used for the expression of NKAF II protein. Plasmid pC1 is a derivative of the plasmid pSV2-dhfr [ATCC Accession No. 37146]. Both plasmids contain the mouse DHFR gene under control of the SV40 early promoter. Chinese hamster ovary- or other cells lacking dihydrofolate activity that are transfected with these plasmids can be selected by growing the cells in a selective medium (alpha minus MEM, Lift Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, J. Biol. Chem. 253:1357–1370, Hamlin, J. L. and Ma, C. 1990, Biochem. et Biophys. Acta, 1097:107–143,Page, M. J. and Sydenham, M. A. 1991, Biotechnology Vol. 9:64–68). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC1 contains for the expression of the gene of interest a strong promoter of the long terminal repeat (LTR) of the Rouse Sarcoma Virus (Cullen, et al., Molecular and Cellular Biology, March 1985, 438–4470) plus a fragment isolated from the enhancer of the immediate early gene of human cytomegalovirus (CMV) (Boshart et al., Cell 41:521–530, 1985). Downstream of the promoter are the following single restriction enzyme cleavage sites that allow the integration of the genes: BamHI, Pvull, and Nrul. Behind these cloning sites the plasmid contains translational stop codons in all three reading frames followed by the 3' intron and the polyadenylation site of the rat preproinsulin gene. Other high efficient promoters can also be used for the expression, e.g., the human β-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosome can also be selected upon co-transfection with a selectable marker such as gpt, G418 or hygromycin. It is advantageous to use more than one selectable marker in the beginning, e.g. G418 plus methotrexate.

The plasmid pC1 is digested with the restriction enzyme BamHI and then dephosphorylated using calf intestinal phosphatase by procedures known in the art. The vector is then isolated from a 1% agarose gel.

The DNA sequence encoding NKAF II, 97465 is amplified using PCR oligonucleotide primers corresponding to the 5' and 3' sequences of the gene:

The 5' primer has the sequence 5' CGC <u>GGATCC</u> GCC ATC ATG CAA CGC CTC TTG 3' (SEQ ID NO:9) containing the underlined Bam HI restriction enzyme site followed by 15 bases of the sequence of NKAF II of FIG. 1 (SEQ ID NO:1). The 3' primer has the sequence 5' CGC <u>GGT ACC</u> CTC CGT GCC GCT GGC TTA 3' (SEQ ID NO:10) containing the underlined Asp718 restriction followed by nucleotides complementary to 18 nucleotides of NKAF II non-coding sequence next to stop codon.

The amplified fragments are isolated from a 1% agarose gel as described above and then digested with the endonuclease BamHI and then purified again on a 1% agarose gel.

The isolated fragment and the dephosphorylated vector are then ligated with T4 DNA ligase. *E.coli* HB101 cells are then transformed and bacteria identified that contained the plasmid pC1 inserted in the correct orientation using the restriction enzyme BamHI. The sequence of the inserted gene is confirmed by DNA sequencing.

Transfection of CHO-DHFR-cells

Chinese hamster ovary cells lacking an active DHFR enzyme are used for transfection. 5 mg of the expression plasmid C1 are cotransfected with 0.5 mg of the plasmid pSVneo using the lipofectin method (Felgner et al., supra). The plasmid pSV2-neo contains a dominant selectable marker, the gene neo from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) and cultivated from 10–14 days. After this period, single clones are trypsinized and then seeded in 6-well petri dishes using different concentrations of methotrexate (25, 50 nm, 100 nm, 200 nm, 400 nm). Clones growing at the highest concentrations of methotrexate are then transferred to new 6-well plates containing even higher concentrations of methotrexate (500 nM, 1 mM, 2 mM, 5 mM). The same procedure is repeated until clones grow at a concentrationof 100 mM.

The expression of the desired gene product is analyzed by Western blot analysis and SDS-PAGE.

It will be clear that the invention may be practiced otherwise than as particularly described in the foregoing description and examples.

What is claimed is:

1. An isolated polynucleotide comprising a nucleotide sequence selected from the group consisting of:
    (a) a nucleotide sequence encoding amino acids −17 to +208 of SEQ ID NO:2;
    (b) a nucleotide sequence encoding amino acids −16 to +208 of SEQ ID NO:2;
    (c) a nucleotide sequence encoding amino acids 1 to 208 of SEQ ID NO:2; and
    (d) a nucleotide sequence encoding amino acids 4 to 208 of SEQ ID NO:2.

2. The isolated polynucleotide of claim 1 wherein said nucleotide sequence is (a).

3. The isolated polynucleotide of claim 1 wherein said nucleotide sequence is (b).

4. The isolated polynucleotide of claim 1 wherein said nucleotide sequence is (c).

5. The isolated polynucleotide of claim 1 wherein said nucleotide sequence is (d).

6. The polynucleotide of claim 1 wherein the polynucleotide further comprises a heterologous polynucleotide sequence.

7. The polynucleotide of claim 6 wherein said heterologous polynucleotide sequence encodes a heterologous polypeptide.

8. A recombinant vector comprising the polynucleotide of claim 1.

9. The recombinant vector of claim 8 wherein the polynucleotide is operably linked to a heterologous regulatory sequence that controls gene expression.

10. A method of producing a recombinant vector comprising inserting the isolated polynucleotide of claim 1 into a vector.

11. A recombinant host cell comprising the isolated polynucleotide of claim 1.

12. The recombinant host cell of claim 11 wherein the polynucleotide is operably linked to a heterologous regulatory sequence that controls gene expression.

13. A recombinant host cell comprising the recombinant vector of claim 8.

14. A method of producing a host cell comprising transducing, transforming or transfecting a host cell with the vector of claim 8.

15. A method for producing a polypeptide, comprising:
   (a) culturing the host cell of claim 12 under conditions producing a polypeptide encoded by said polynucleotide; and
   (b) recovering said polypeptide.

16. A composition comprising the polynucleotide of claim 1 and a pharmaceutically acceptable carrier.

17. An isolated polynucleotide comprising a nucleotide sequence selected from the group consisting of:
   (a) a nucleotide sequence encoding the fiull-length polypeptide encoded by the cDNA contained in ATCC Deposit No. 97465; and
   (b) a nucleotide sequence encoding a mature polypeptide encoded by the cDNA contained in ATCC Deposit No. 97465.

18. The isolated polynucleotide of claim 17 wherein said nucleotide sequence is (a).

19. The isolated polynucleotide of claim 17 wherein said nucleotide sequence is (b).

20. The polynucleotide of claim 17 wherein the polynucleotide further comprises a heterologous polynucleotide sequence.

21. The polynucleotide of claim 20 wherein said heterologous polynucleotide sequence encodes a heterologous polypeptide.

22. A recombinant vector conprising the polynucleotide of claim 17.

23. The recombinant vector of claim 22 wherein the polynucleotide is operably linked to a heterologous regulatory sequence that controls gene expression.

24. A method of producing a recombinant vector comprising inserting the isolated polynucleotide of claim 17 into a vector.

25. A recombinant host cell comprising the isolated polynucleotide of claim 17.

26. The recombinant host cell of claim 25 wherein the polynucleotide is operably linked to a heterologous regulatory sequence that controls gene expression.

27. A recombinant host cell comprising the recombinant vector of claim 22.

28. A method of producing a host cell comprising transducing, transforming or transfecting a host cell with the vector of claim 22.

29. A method for producing a polypeptide, comprising:
   (a) culturing the host cell of claim 26 under conditions producing a polypeptide encoded by said polynucleotide; and
   (b) recovering said polypeptide.

30. A composition comprising the polynucleotide of claim 17 and a pharmaceutically acceptable carrier.

31. An isolated polynucleotide comprising a nucleotide sequence 90% or more identical to a nucleotide sequence selected from the group consisting of:
   (a) a nucleotide sequence encoding amino acids −17 to +208 of SEQ ID NO:2;
   (b) a nucleotide sequence encoding amino acids −16 to 208 of SEQ ID NO:2;
   (c) a nucleotide sequence encoding amino acids 1 to 208 of SEQ ID NO:2; and
   (d) a nucleotide sequence encoding amino acids 4 to 208 of SEQ ID NO:2;
   wherein the polypeptide encoded by said polynucleotide comprises an antigenic fragment of SEQ ID NO:2.

32. The isolated polynucleotide of claim 31 wherein said second nucleotide sequence is (a).

33. The isolated polynucleotide of claim 31 wherein said second nucleotide sequence is (b).

34. The isolated polynucleotide of claim 31 wherein said second nucleotide sequence is (c).

35. The isolated polynucleotide of claim 31 wherein said second nucleotide sequence is (d).

36. The polynucleotide of claim 31 wherein the polynucleotide further comprises a heterologous polynucleotide sequence.

37. The polynucleotide of claim 36 wherein said heterologous polynucleotide sequence encodes a heterologous polypeptide.

38. A recombinant vector comprising the polynucleotide of claim 31.

39. The recombinant vector of claim 38 wherein the polynucleotide is operably linked to a heterologous regulatory sequence that controls gene expression.

40. A method of producing a recombinant vector comprising inserting the isolated polynucleotide of claim 31 into a vector.

41. A recombinant host cell comprising the isolated polynucleotide of claim 31.

42. The recombinant host cell of claim 41 wherein the polynucleotide is operably linked to a heterologous regulatory sequence that controls gene expression.

43. A recombinant host cell comprising the recombinant vector of claim 38.

44. A method of producing a host cell comprising tansducing, tranforming or transfecting a host cell with the vector of claim 38.

45. A method for producing a polypeptide, comprising:
   (a) culturing the host cell of claim 42 under conditions producing a polypeptide encoded by said polynucleotide; and
   (b) recovering said polypeptide.

46. A composition comprising the polynucleotide of claim 31 and a pharmaceutically acceptable carrier.

47. An isolated polynucleotide comprising a nucleotide sequence 90% or more identical to a nucleotide sequence selected from the group consisting of:
   (a) a nucleotide sequence encoding the full-length polypeptide encoded by the cDNA contained in ATCC Deposit No. 97465; and
   (b) a nucleotide sequence encoding a mature polypeptide encoded by the cDNA contained in ATCC Deposit No. 97465;
   wherein the polypeptide encoded by said polynucleotide comprises an antigenic fragment of SEQ ID NO:2.

48. The isolated polynucleotide of claim 42 wherein said second nucleotide sequence is (a).

49. The isolated polynucleotide of claim 47 wherein said second nucleotide sequence is (b).

50. The polynucleotide of claim 47 wherein the polynucleotide further comprises a heterologous polynucleotide sequence.

51. The polynucleotide of claim 50 wherein said heterologous polynucleotide sequence encodes a heterologous polypeptide.

52. A recombinant vector comprsing the polynucleotide of claim 47.

53. The recombinant vector of claim 52 wherein the polynucleotide is operably linked to a heterologous regulatory sequence that controls gene expression.

54. A method of producing a recombinant vector comprising inserting the isolated polynucleotide of claim 47 into a vector.

55. A recombinant host cell comprising the isolated polynucleotide of claim 47.

56. The recombinant host cell of claim 55 wherein the polynucleotide is operably linked to a heterologous regulatory sequence that controls gene expression.

57. A recombinant host cell comprising the recombinant vector of claim 52.

58. A method of producing a host cell comprising transducing, transforming or transfecting a host cell with the vector of claim 52.

59. A method for producing a polypeptide, comprising:
(a) culturing the host cell of claim 56 under conditions producing a polypeptide encoded by said polynucleotide; and
(b) recovering said polypeptide.

60. A composition comprising the polynucleotide of claim 47 and a pharmaceutically acceptable carrier.

61. An isolated polynucleotide comprising at least 30 contiguous nucleotides of coding sequence in SEQ ID NO:1, or the complementary strand thereto.

62. The isolated polynucleotide of claim 61 wherein said polynucleotide comprises at least 30 contiguous nucleotides of coding sequence in SEQ ID NO:1.

63. The isolated polynucleotide of claim 61 wherein said polynucleotide comprises at least 30 contiguous nucleotides of the complementary strand of the coding sequence in SEQ ID NO:1.

64. The isolated polynucleotide of claim 61 wherein said polynucleotide comprises at least 50 contiguous nucleotides of coding sequence in SEQ ID NO:1.

65. The isolated polynucleotide of claim 61 wherein said polynucleotide comprises at least 50 contiguous nucleotides of the complementary strand of the coding sequence in SEQ ID NO:1.

66. The isolated polynucleotide of claim 61 wherein said polynucleotide comprises nucleotides 147 to 756 of SEQ ID NO:1.

67. The isolated polynucleotide of claim 61 wherein said polynucleotide comprises nucleotides 133 to 756 of SEQ ID NO:1.

68. The isolated polynucleotide of claim 61 wherein said polynucleotide comprises nucleotides 82 to 857 of SEQ ID NO:1.

69. The isolated polynucleotide of claim 61 wherein said polynucleotide comprises nucleotides 1 to 857 of SEQ ID NO:1.

70. The isolated polynucleotide of claim 64 wherein said polynucleotide comprises the full-length coding sequence in SEQ ID NO:1.

71. The isolated polynucleotide of claim 61 wherein said polynucleotide comprises the complementary strand of the full-length coding sequence in SEQ ID NO:1.

72. The polynucleotide of claim 61 wherein the polynucleotide further comprises a heterologous polynucleotide sequence.

73. The polynucleotide of claim 72 wherein said heterologous polynucleotide sequence encodes a heterologous polypeptide.

74. A recombinant vector comprising the polynucleotide of claim 61.

75. The recombinant vector of claim 74 wherein the polynucleotide is operably linked to a heterologous regulatory sequence that controls gene expression.

76. A method of producing a recombinant vector comprising inserting the isolated polynucleotide of claim 61 into a vector.

77. A recombinant host cell comprising the isolated polynucleotide of claim 61.

78. The recombinant host cell of claim 71 wherein the polynucleotide is operably linked to a heterologous regulatory sequence that controls gene expression.

79. A recombinant host cell comprising the recombinant vector of claim 74.

80. A method of producing a host cell comprising transducing, transforming or transfecting a host cell with the vector of claim 74.

81. A method for producing a polypeptide, comprising:
(a) culturing the host cell of claim 78 under conditions producing a polypeptide encoded by said polynucleotide; and
(b) recovering said polypeptide.

82. A composition comprising the polynucleotide of claim 61 and a pharmaceutically acceptable carrier.

83. An isolated polynucleotide comprising at least 30 contiguous nucleotides of coding sequence of the cDNA contained in ATCC Deposit No. 97465, or the complementary strand thereto.

84. The isolated polynucleotide of claim 83 wherein said polynucleotide comprises at least 30 contiguous nucleotides of the coding sequence of the cDNA contained in ATCC Deposit No. 97465.

85. The isolated polynucleotide of claim 83 wherein said polynucleotide comprises at least 30 contiguous nucleotides of the complementary strand of the coding sequence of the cDNA contained in ATCC Deposit No. 97465.

86. The isolated polynucleotide of claim 83 wherein said polynucleotide comprises at least 50 contiguous nucleotides of the coding sequence of the cDNA contained in ATCC Deposit No. 97465.

87. The isolated polynucleotide of claim 83 wherein said polynucleotide comprises at least 50 contiguous nucleotides of the complementary strand of the coding sequence of the cDNA contained in ATCC Deposit No. 97465.

88. The isolated polynucleotide of claim 83 wherein said polynucleotide comprises the full-length coding sequence of the cDNA contained in ATCC Deposit No. 97465.

89. The isolated polynucleotide of claim 83 wherein said polynucleotide comprises the complementary strand of the full-length coding sequence of the cDNA contained in ATCC Deposit No. 97465.

90. The polynucleotide of claim 83 wherein the polynucleotide further comprises a heterologous polynucleotide sequence.

91. The polynucleotide of claim 90 wherein said heterologous polynucleotide sequence encodes a heterologous polypeptide.

92. A recombinant vector comprising the polynucleotide of claim 83.

93. The recombinant vector of claim 92 wherein the polynucleotide is operably linked to a heterologous regulatory sequence that controls gene expression.

94. A method of producing a recombinant vector comprising inserting the isolated polynucleotide of claim 83 into a vector.

95. A recombinant host cell comprising the isolated polynucleotide of claim 83.

96. The recombinant host cell of claim 95 wherein the polynucleotide is operably linked to a heterologous regulatory sequence that controls gene expression.

97. A recombinant host cell comprising the recombinant vector of claim 92.

98. A method of producing a host cell comprising transducing, transforming or transfecting a host cell with the vector of claim 92.

99. A method for producing a polypeptide, comprising:
(a) culturing the host cell of claim 96 under conditions producing a polypeptide encoded by said polynucleotide; and
(b) recovering said polypeptide.

100. A composition comprising the polynucleotide of claim 83 and a pharmaceutically acceptable carrier.

101. An isolated polynucleotide comprising a nucleotide sequence encoding at least 30 contiguous amino acids of SEQ ID NO:2, wherein the polypeptide encoded by said polynucleotide comprises an antigenic fragment of SEQ ID NO:2.

102. The isolated polynucleotide of claim 101 which comprises a nucleotide sequence encoding at least 50 contiguous amino acids of SEQ ID NO:2.

103. The polynucleotide of claim 101 wherein the polynucleotide further comprises a heterologous polynucleotide sequence.

104. The polynucleotide of claim 103 wherein said heterologous polynucleotide sequence encodes a heterologous polypeptide.

105. A recombinant vector comprising the polynucleotide of claim 101.

106. The recombinant vector of claim 105 wherein the polynucleotide is operably linked to a heterologous regulatory sequence that controls gene expression.

107. A method of producing a recombinant vector comprising inserting the isolated polynucleotide of claim 101 into a vector.

108. A recombinant host cell comprising the isolated polynucleotide of claim 101.

109. The recombinant host cell of claim 108 wherein the polynucleotide is operably linked to a heterologous regulatory sequence that controls gene expression.

110. A recombinant host cell comprising the recombinant vector of claim 105.

111. A method of producing a host cell comprising transducing, transforming or transfecting a host cell with the vector of claim 105.

112. A method for producing a polypeptide, comprising:
(a) culturing the host cell of claim 109 under conditions producing a polypeptide encoded by said polynucleotide; and
(b) recovering said polypeptide.

113. A composition comprising the polynucleotide of claim 101 and a pharmaceutically acceptable carrier.

114. An isolated polynucleotide comprising a nucleotide sequence encoding at least 30 contiguous amino acids of a nucleotide sequence encoding the full-length polypeptide encoded by the cDNA contained in ATCC Deposit No. 97465, wherein the polypeptide encoded by said polynucleotide comprises an antigenic fragment of SEQ ID NO:2.

115. The isolated polynucleotide of claim 114 which comprises a nucleotide sequence encoding at least 50 contiguous amino acids of a nucleotide sequence encoding the full-length polypeptide encoded by the cDNA contained in ATCC Deposit No. 97465.

116. The polynucleotide of claim 114 wherein the polynucleotide further comprises a heterologous polynucleotide sequence.

117. The polynucleotide of claim 116 wherein said heterologous polynucleotide sequence encodes a heterologous polypeptide.

118. A recombinant vector comprising the polynucleotide of claim 114.

119. The recombinant vector of claim 118 wherein the polynucleotide is operably linked to a heterologous regulatory sequence that controls gene expression.

120. A method of producing a recombinant vector comprising inserting the isolated polynucleotide of claim 114 into a vector.

121. A recombinant host cell comprising the isolated polynucleotide of claim 114.

122. The recombinant host cell of claim 121 wherein the polynucleotide is operably linked to a heterologous regulatory sequence that controls gene expression.

123. A recombinant host cell comprising the recombinant vector of claim 118.

124. A method of producing a host cell comprising transducing, transforming or transfecting a host cell with the vector of claim 118.

125. A method for producing a polypeptide, comprising:
(a) culturing the host cell of claim 122 under conditions producing a polypeptide encoded by said polynucleotide; and
(b) recovering said polypeptide.

126. A composition comprising the polynucleotide of claim 114 and a pharmaceutically acceptable carrier.

127. An isolated polynucleotide comprising a nucleotide sequence which hybridizes to the complementary stand of the coding sequence of the cDNA contained in ATCC Deposit No. 97465, wherein said hybridization occurs under conditions consisting of hybridization in a buffer consisting of 7% SDS and 0.5 M NaPO4 (pH 7.6) at 65° C. and wash in a solution consisting of 0.5×SSC at 60° C.

128. The polynucleotide of claim 127 wherein the polynucleotide further comprises a heterologous polynucleotide sequence.

129. The polynucleotide of claim 128 wherein said heterologous polynucleotide sequence encodes a heterologous polypeptide.

130. A recombinant vector comprising the polynucleotide of claim 127.

131. The recombinant vector of claim 130 wherein the polynucleotide is operably linked to a heterologous regulatory sequence that controls gene expression.

132. A method of producing a recombinant vector comprising inserting the isolated polynucleotide of claim 127 into a vector.

133. A recombinant host cell comprising the isolated polynucleotide of claim 127.

134. The recombinant host cell of claim 133 wherein the polynucleotide is operably linked to a heterologous regulatory sequence that controls gene expression.

135. A recombinant host cell comprising the recombinant vector of claim 130.

136. A method of producing a host cell comprising transducing, transforming or transfecting a host cell with the vector of claim 130.

137. A method for producing a polypeptide, comprising:
(a) culturing the host cell of claim 134 under conditions producing a polypeptide encoded by said polynucleotide; and
(b) recovering said polypeptide.

138. A composition comprising the polynucleotide of claim 127 and a pharmaceutically acceptable carrier.

* * * * *